US007354755B2

(12) United States Patent
Zhang et al.

(10) Patent No.: US 7,354,755 B2
(45) Date of Patent: *Apr. 8, 2008

(54) STABLE ZYMOMONAS MOBILIS XYLOSE AND ARABINOSE FERMENTING STRAINS

(75) Inventors: Min Zhang, Lakewood, CO (US); Yat-Chen Chou, Taipei (TW)

(73) Assignee: Midwest Research Institute, Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/565,233

(22) Filed: May 1, 2000

(65) Prior Publication Data

US 2002/0151034 A1 Oct. 17, 2002

(51) Int. Cl.
*C12N 1/21* (2006.01)
*C12N 15/00* (2006.01)
*C12N 15/11* (2006.01)

(52) U.S. Cl. .............................. 435/252.3; 435/320.1; 536/23.1

(58) Field of Classification Search ............. 435/320.1, 435/252.3, 161, 165; 536/23.2
See application file for complete search history.

(56) References Cited

U.S. PATENT DOCUMENTS

| 5,514,583 A |   | 5/1996  | Picataggio ............... 435/252.3 |
| 5,712,133 A | * | 1/1998  | Picataggio et al. ......... 435/161 |
| 5,726,053 A | * | 3/1998  | Picataggio et al. ...... 435/252.3 |
| 5,843,760 A |   | 12/1998 | Zhang ..................... 435/252.3 |

FOREIGN PATENT DOCUMENTS

| WO | WO 97/42307    | 11/1997 |
| WO | WO 98/50524    | 11/1998 |
| WO | WO 01/83784 A2 | 11/2001 |

OTHER PUBLICATIONS

Deanda et al. 1996. Applied and Environmental Microbiology 62:4465-4470.*
Herrero et al. 1990. Journal of Bacteriology 172:6557-6567.*
De Lorenzo et al. 1990, Journal of Bacteriology. 172:6568-6572.*
Pappas et al. 1997. Journal of Applied Microbiology. 82:379-388.*
Yomano et al. 1993. Journal of Bacteriology 175: 3926-3933.*
Quandt et al. 1993. Gene 127:15-21.*
Suzuki et al. 1986. An Introduction to Genetic Analysis. W.H. Freeman and Co., New York. p. 386.*
Chou et al. Abstracts of the General Meeting of the American Society for Microbiology, 1999. vol. 99, p. 370.*
"Improve Symomonas for Xylose and Arabinose Fermentation" 1998-99 Office of Fuels Development Project Summaries, Fermentation Organism Development, Online, Mar. 2000, XP002184798. Retrieved from the Internet: http://bioenergy.oml.gov/99summaries/fermentation.html.*
Zhang et al , "Genetic Improvement of Zymomonas mobilis for Ethanol Production: Chromosomal Integration of the Xylose- and Arabinose-Fermentating Genes" 22nd Symposium on Biotechnology for Fuels and Chemicals, Online Mar. 24, 2000, XP002184800 Retrieved from the Internet: URL:http://www.ct.ornl.gov/symposium/22nd/index_files/oral02.0.html.*
Pappas, K. M., et al., Transposon mutagenesis and strain construction in *Zymomonas mobilis*, Journal of Applied Microbiology 82:379-388, 1997.
DeLorenzo, V., et al., Mini-Tn5 Transposon Derivatives for Insertion Mutagenesis, Promoter Probing, and Chromosomal Insertion of Cloned DNA in Gram-negative Eubacteria, Journal of Bacteriology, vol. 172, No. 11, p. 6568-6572, 1990.
Herrero, M., et al., Transposon Vectors Containing Non-Antibiotic Resistance Selection Markers for Cloning and Stable Chromosomal Insertion of Foreign Genes in Gram-negative Bacteria, Journal of Bacteriology, vol. 172, No. 11, p. 6557-6567, 1990.
Fellay, R., et al., Interposon mutagenesis of soil and water bacteria a family of DNA fragments designed for in vitro insertional mutagenesis of Gram-negative bacteria, Gene, vol. 52., pp. 147-154, 1987.
Dodson, Karen W., et al., Factors affecting transposition activity of IS50 and Tn5 ends, Gene, vol. 76, pp. 207-213, 1989.
Auerswald, E.A., et al., Structural analysis of Tn5, Cold Springs Harbor Symp. Quant. Biol. vol. 45 pp. 107-113, 1980.
Yomano, L.P., et al., Cloning, sequencing, and expression of the *Zymomonas mobilis* phosphoglycerate mutase gene (pgm) in *Escherichia coli*, Journal of Bacteriology, vol. 175, pp. 3926-3933, 1993.
Deanda, K.A., et al., Development of an arabinose-fermenting *Zymomonas mobilis* strain by metabolic pathway engineering, Journal of Applied and Environmental Microbiology, vol. 62, pp. 4465-4470, 1996.
Zhang, K., et al., Metabolic engineering of a pentose metabolism pathway in ethanologenic *Zymomonas mobilis*, Science, vol. 267, pp. 240-243, 1995.

(Continued)

*Primary Examiner*—Nancy Vogel
(74) *Attorney, Agent, or Firm*—Paul J. White; Kenneth Richardson; Mark D. Trenner

(57) ABSTRACT

The present invention briefly includes a transposon for stable insertion of foreign genes into a bacterial genome, comprising at least one operon having structural genes encoding enzymes selected from the group consisting of xylAxylB, araBAD and tal/tkt, and at least one promoter for expression of the structural genes in the bacterium, a pair of inverted insertion sequences, the operons contained inside the insertion sequences, and a transposase gene located outside of the insertion sequences. A plasmid shuttle vector for transformation of foreign genes into a bacterial genome, comprising at least one operon having structural genes encoding enzymes selected from the group consisting of xylAxylB, araBAD and tal/tkt, at least one promoter for expression of the structural genes in the bacterium, and at least two DNA fragments having homology with a gene in the bacterial genome to be transformed, is also provided.

The transposon and shuttle vectors are useful in constructing significantly different *Zymomonas mobilis* strains, according to the present invention, which are useful in the conversion of the cellulose derived pentose sugars into fuels and chemicals, using traditional fermentation technology, because they are stable for expression in a non-selection medium.

6 Claims, 18 Drawing Sheets

OTHER PUBLICATIONS

"Improve *Zymomonas* for Xylose and Arabinsose Fermentation" 1998-99 Office of Fuels Developement Project Summaries, Fermentation Organism Development, Online! Mar. 2000, XP002184798 Retrieved from the Internet: <URL:http://bioenergy.ornl.gov/99summaries/fermentation.html>.

Chou, Y.C. et al.: "Inactivation of the D-lactate dehydrogenase gene in *Zymomonas mobilis* through homologous recombination" Abstracts of the General Meeting of the American Society For, vol. 99, 1999, p. 370 XP00284799, 99th General Meeting of the American Society for Microbiology; Chicago, Illinois, USA; May 30-Jun. 3, 1999, ISSN: 1060-2011.

Zhang, M. et al. : "Genetic Improvement of *Zymomonas mobilis* for Ethanol Production: Chromosomal Integration of the Xylose-And Arabinose-Fermenting Genes" 22nd Symposium on Biotechnology for Fuels and Chemicals, May 7-10, 2000, Online! Mar. 24, 2000, XP002184800 Retrieved from the Internet: <URL:http://www.ct.ornl.gov/symposium/22nd/index_files/oral02.0.html>.

Bejar, S. et al.: "Construction of a new strain of *Streptomyces violaceoniger*, having strong, constitutive and stable glucose-isomerase activity" Biotechnology Letters, vol. 16, No. 12, 1994, pp. 1259-1265, XP001041576 ISSN: 0141-5492.

Lawford, Hugh G. et al.: "Fermentation performance assessment of a genomically integrated xylose-utilizing recombinant of *Zymomonas mobilis* 39676" Applied Biochemistry and Biotechnology, vol. 91-93, Apr. 1, 2001, pp. 117-131, XP001041535 ISSN: 0273-2289.

* cited by examiner

*Z. mobilis* Strains

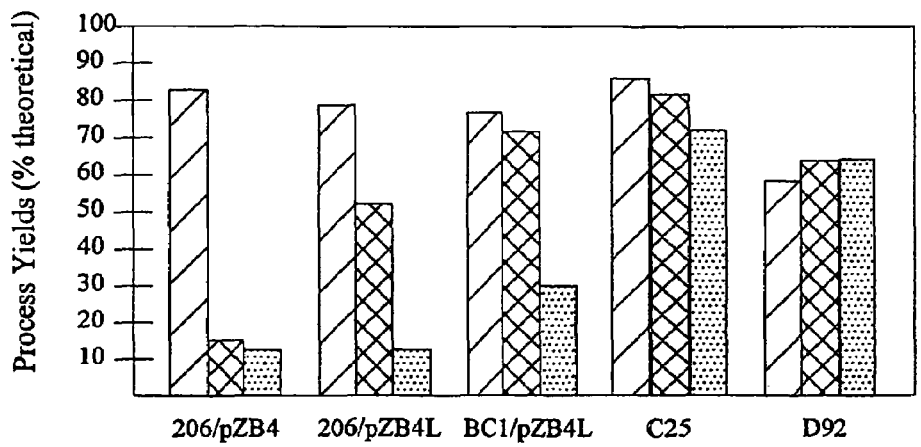
FIG. 8A
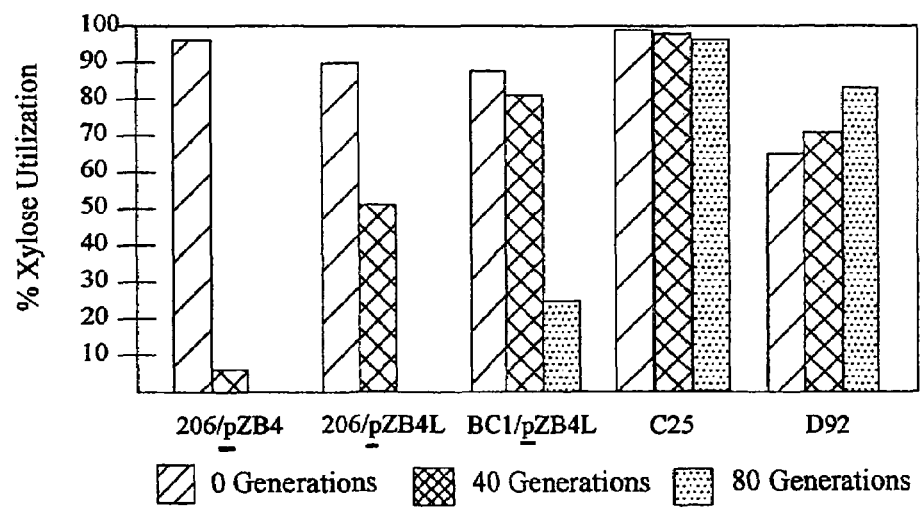
FIG. 8B
FIG. 8

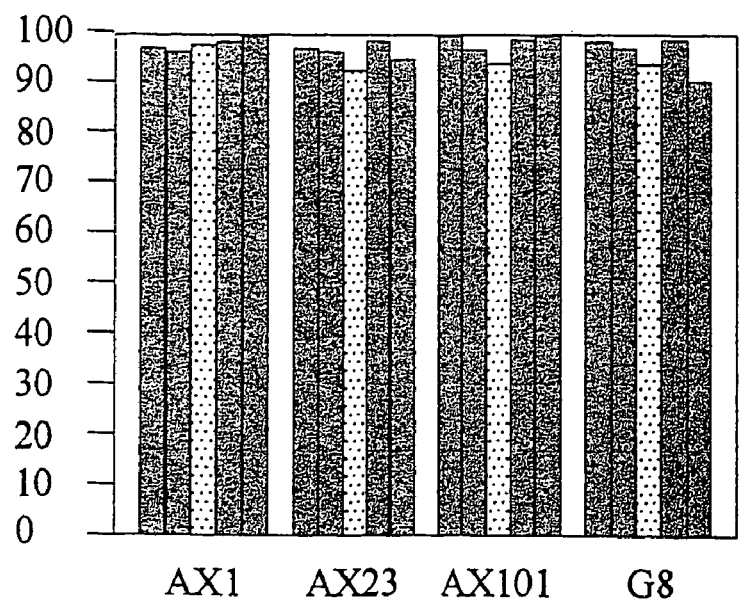
FIG. 17A
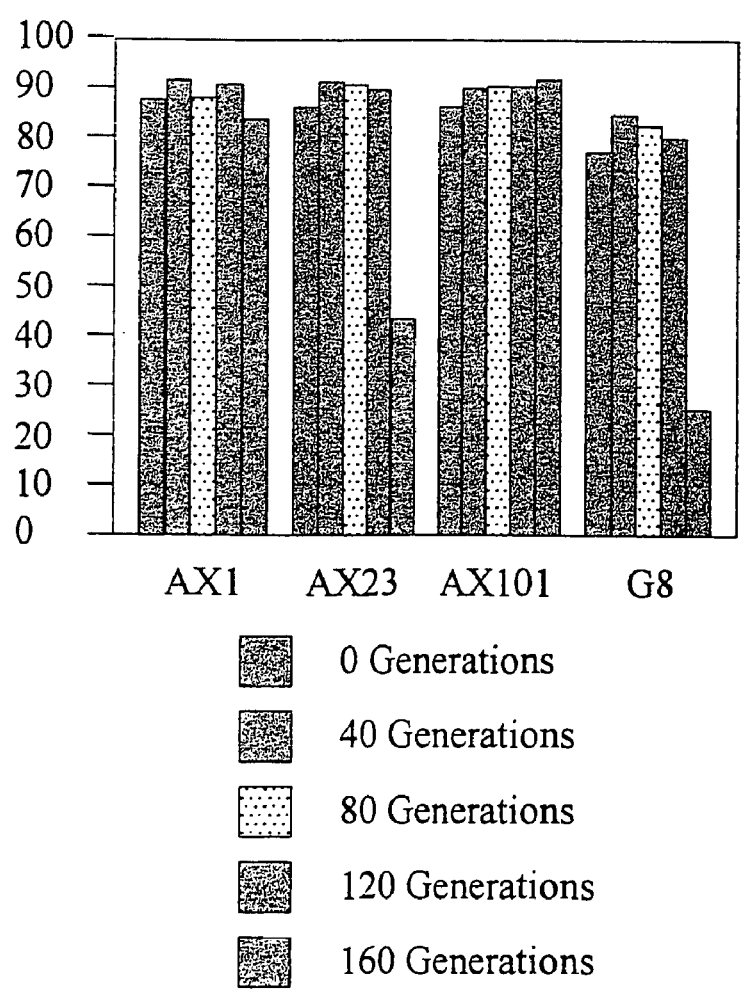
FIG. 17B
FIG. 17

SEQUENCE LISTING

```
<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Tc primer
      for DNA labeling

<400> SEQUENCE: 1
ttgctaacgc agtcaggc                                                  18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Tc primer
      for DNA labeling

<400> SEQUENCE: 2
gaatccgtta gcgaggtg                                                  18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: xylB primer
```

-continued used for DNA labeling

<400> SEQUENCE: 3
tatgggttca gcggcatgag                                                    20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: xylB primer
      for DNA labeling

<400> SEQUENCE: 4
atgggcatga gatccatagc c                                                  21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Tnp primer
      for DNA labeling

<400> SEQUENCE: 5
tcctaacatg gtaacgttc                                                     19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Tnp primer
      for DNA labeling

<400> SEQUENCE: 6
ccaaccttac cagagggc                                                      18

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Tal primer
      for DNA labeling

<400> SEQUENCE: 7
cgtctaaaag attttaagaa aggtttcgat atgacggaca aattgacc                     48

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Tal primer
      for DNA labeling

<400> SEQUENCE: 8
cattttgact ccagatctag attacagcag atcgccgatc attttttcc                    49

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Primer for
      amplification of ldhL gene fragment using PCR

<400> SEQUENCE: 9
tcgcggatcc tctatcccctt tattttttcta tccccatcac ctcgg    45

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Primer for
      amplification of ldhL gene fragment using PCR

<400> SEQUENCE: 10
tcgcggatcc gcggctgaca tacatcttgc gaatataggg    40

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Primer for
      amplification of DIG-ldh gene fragment using PCR

<400> SEQUENCE: 11
tcgcggatcc gtctatgcgc gtcgcaatat tcagttcc    38

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Primer for
      amplification of DIG labeled ldhL gene fragment using PCR

<400> SEQUENCE: 12
tcgcggatcc gtcgcttgtc tattaaacaa gcgcatccgg c    41

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Primer for
      amplification of DIG labeled ara gene fragment using PCR

<400> SEQUENCE: 13
ctaacatgtt gactccttct ctagacttag cg    32

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Primer for
      amplification of DIG labeled ara gene fragment using PCR

<400> SEQUENCE: 14
gttgaaaccg ctgggcacca cgc    23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer for
      amplification of DIG labeled tnp gene fragment using PCR -continued

```
<400> SEQUENCE: 15
cgcactacac ggtcgttctg ttac                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer for
      amplification of DIG labeled tnp gene fragment using PCR

<400> SEQUENCE: 16
ggttgcagcc acgagtaagt cttc                                              24
```

STABLE ZYMOMONAS MOBILIS XYLOSE AND ARABINOSE FERMENTING STRAINS

The United States Government has rights in this invention pursuant to Contract No. DE-AC36-83CH10093 between the United States Department of Energy and Midwest Research Institute.

BACKGROUND OF THE INVENTION

1. Field of the Invention

The present invention relates to the biological conversion of cellulosic substrates into fuels and chemicals, and in particular to recombinant *Zymomonas mobilis* strains which ferment xylose and arabinose, or both, into ethanol.

2. Description of the Related Art

Fermentation technology is useful for the conversion renewable biomass cellulose substrates into fuels and chemicals, such as ethanol. A typical substrate is comprised of 35-45% cellulose, 30-40% hemicellulose, and 15% lignin. The hydrolysis fraction contains glucose polymers, and the hemicellulose fraction contains mostly xylose. Arabinose is also a significant fermentable substrate found in biomass materials, such as switchgrass grass and corn fiber. Thus, achieving a high rate of specific product formation and conversion efficiency in the fermentation of the pentose sugars is vital to the commercial production of fuels and chemicals from a renewable substrates.

*Z. mobilis* is widely reported for its ability to rapidly and efficiently convert glucose substrates into ethanol, at a low pH, in an anaerobic culture, and in a medium which contains the inhibitory compounds typically associated with a lignocellulose-hydrolysate. A distinct disadvantage in the use of *Z. mobilis* is, however, that it does not ferment pentose sugars. To overcome this disadvantage, the prior art has focused on recombinant *Z. mobilis* strains which ferment a mixture of glucose, and xylose or arabinose, or both, using exogenous genes which catalyze the metabolism of xylose and arabinose. These strains, and the cloning vectors, are based on the use of multiple-copy plasmids having antibiotic resistance markers.

U.S. Pat. No. 5,514,583 discloses a transformed *Z. mobilis* xylose fermenting strain (CP4/pZB4 and pZB5) having exogenous genes, and plasmid vectors (pZB4 and pZB5) encoding xylose isomerase, xylulokinase, transaldolase and transketolase, and further comprising at least one promoter (Pgap and Peno) recognized by *Zymomonas* which regulates the expression of at least one of said genes. The microorganism is capable of growing on xylose as a sole carbon source, and fermenting xylose to ethanol at about 88% of the maximum theoretic yield. The patent claims an integrated strain.

U.S. Pat. Nos. 5,712,133 and 5,726,053 disclose, inter alia, *Z. mobilis* arabinose fermenting transformants (39676/pZB 206), containing exogenous genes that encode L-arabinose isomerase, L-ribulokinase and L-ribulose-5-phosphate-4-epimerase, transaldolase and transketolase which impart arabinose to ethanol fermentation capability. The plasmid vector (pZB 206) and a process of using the transformants for the fermentation of a glucose and arabinose containing substrate is also disclosed. The patent claims integration of the exogenous genes into the host genome.

U.S. Pat. No. 5,843,760 discloses a *Z. mobilis* xylose and arabinose fermenting transformant (206C/pZB301) containing exogenous genes encoding xylose isomerase, xylulokinase, L-arabinose isomerase, L-ribulokinase, L-ribulose-5-phosphate 4-epimerase, transaldolase and transketolase, and further comprising at least one promoter recognized by *Zymomonas* which regulates the expression of at least one of said genes, wherein said microorganism is capable of growing on arabinose and/or xylose, alone or in combination, as the carbon source and fermenting said arabinose and xylose to ethanol. The process of using the transformants together with the plasmid vectors (pZB301, pZB401, pZB402, and pZB 403) is also disclosed. This patent claims integration of the exogenous genes into the host genome.

Although hybrid plasmids may be readily maintained in *Z. mobilis* when cultivated in mono-culture under controlled conditions, they frequently become unstable when the host organism is grown in the absence of selection pressure for plasmid maintenance, i.e., in the presence of antibiotics. For example, the exogenous genes in the above referenced strains are capable of stable expression for about forty generations. Instability may be exacerbated when *Z. mobilis* has to compete with other organisms in a mixed culture, such as a cellulose simultaneous-saccharification-fermentation process. In addition, antibiotic resistance markers are generally perceived as undesirable for industrial application, such as the large-scale production of ethanol. Thus, it is preferable to insert the cloned genes into the *Z. mobilis* genome, where they are maintained at a low, natural copy number, and are thus not over-expressed, and where, at least theoretically, they should be as stable as genomic DNA.

In *Escherichia coli*, the classical method for generating genomic inserts of foreign genes involves the use of specialized λ phage cloning vectors that can exist stable in the lysogenic state. Alternatively, genes can be inserted through homologous recombination, when bracketed with *E. coli* chromosomal sequences, or by transposition if the genes can be cloned in the permissive sites of a transposon. While transposition has been demonstrated in *Z. mobilis*, Pappas, K. M., et al., (1997) Transposon mutagensesis and strain construction in *Zymomonas mobilis*, *Journal of Applied Microbiology*, Vol. 82, p.p. 379-388, it has been limited to mini Mμ or Tn5 multiple transposition of random auxotrophy or antibiotic resistance phenotypes for genetic analysis, and in the case of the Tn5 derivatives the insertions are reportedly stable for only 5-15 generations. Pappas, K. M., et seq. P. 383, FIG. 1. Moreover, site-specific insertion through homologous recombination in *Z. mobilis* has not been demonstrated, and no bacteriophage has ever been isolated from *Zymomonas*.

Transposons Tn5 and Tn10 are well known and have been widely used for mutagensis and insertion of cloned DNA into a variety of gram-negative bacteria. In Herrero, M., et al., (1990) Transposon vectors containing non-antibiotic resistance selection markers for cloning and stable chromosomal insertion of foreign genes in gram-negative bacteria, *J. Bacteriol.* 172:6557-6567, a procedure is disclosed for cloning and stable insertion of foreign genes into the chromosome of gram-negative eubacteria by combining two sets of plasmids, (i) the transposition features of Tn10 and Tn5, (ii) the resistance to certain compounds, and (iii) the suicide delivery properties of the R6K-based plasmid pGP704. The resulting constructions contain unique NotI or SfiI sites internal to either the Tn10 or the Tn5 inverted repeats. These sites are used for cloning DNA fragments with the help of two additional specialized cloning plasmids, pUC18Not and pUC18Sfi. The newly derived constructions are maintained only in donor host strains that produce the R6K-specified π protein, which is an essential replication protein for R6K and plasmids derived therefrom. Donor plasmids containing hybrid transposons are transformed into a specialized λpri lysogenic *E. coli* strain, such as *E. coli* Sm10(λpir), with a chromosomally integrated RP4 that provided broad-host range conjugal transfer functions. Delivery of the donor plasmids into selected host bacteria is accomplished through mating with the target strain. Transposition of the hybrid transposon from the delivered suicide plasmid to a replicon in the target is mediated by the cognate transposase encoded on the plasmid at a site external to the transposon. Since the transposase function is not maintained in target cell, such cells are immune to further transposition rounds. Multiple insertions in the same strain are therefore only limited by the availability of distinct selection markers.

Further disclosed in Herrero, M. et al., 1990, Mini-Tn5 Transposon Derivatives for Insertion Mutagenesis Promoter Probing, and Genomic Insertion of Cloned DNA in Gram-Negative Eubacteria, *Journal of Bacteriol. Vol* 172, No. 11, p. 6568-6572, is the construction of a collection of TnS-derived minitransposons, such as Tn5Tc, that enables the introduction of foreign DNA fragments into the chromosome of a variety of gram-negative bacteria. The minitransposons consist of genes specifying the resistance to kanamycin, and tetracycline as selection markers and a unique NotI cloning site flanked by 19-base-pair terminal repeat sequences of Tn5. The transposons are located on a R6K-based suicide delivery plasmid that provides the $IS50_R$ transposase tnp gene in cis but external to the mobile element and whose conjugal transfer to recipients is mediated by RP4 mobilization functions in the donor. Therefore, insertions produced by these elements are generally more stable because of the absence of transposase-mediated secondary transpositions, deletions, and inversions. See also, Berg et al., (1989) Transposable elements and the genetic engineering of bacteria, p.p. 879-926, in D. E. Berg, *Mobile DNA*, American Society for Microbiology, Washington, D.C. Very stable insertions can in this way be obtained with elements derived, for instance also from Tn10. Way, J. C. et al., (1984) New Tn10 derivatives for transposon mutagenesis and for construction of lacZ operon fusions by transposition. *Gene* 32: 369-379.

The structure of mini-TnSTc, Herrero, et seq., p. 6569, is disclosed for use for insertion mutagenesis or as a transposon vector for the cloning of DNA fragments flanked by NotI sites (readily isolated by cloning DNA fragments first into the pUC18 derivatives pUC18Not and pUC18Not). The Mini-Tn5Tc element is constructed, in vitro, using standard recombinant DNA techniques. Maniatis, T., et al., (1989) *Molecular cloning: a laboratory manual*, Cold Spring Harbor Laboratory, Cold Spring Harbor, N.Y. The determinant for tetracycline (Tc) resistance is obtained as an EcoRI fragment from plasmids bearing them as an interposon. Fellay, R., et al. (1987) Interposon mutagensesis of soil and water bacteria: a family of DNA fragments designed for in vitro insertion mutagenesis of Gram-negative bacteria, *Gene* 52: 147-154. This fragments is subsequently cloned into the single EcoRI site of pUC18Sfi, excised as an SfiI fragment, and inserted between the Tn5 19-base pair termini in pUT so that the mobile unit is present in all cases as an XbaI-EcoRI (partial) portion of the delivery plasmid. The resulting element is mini-Tn5Tc.

Tn10-based transposon vector delivery systems are described in Herrero, M., et seq. 172:6557-6567. Phageλ, a derivative λRP167, carries a 5.1-kb EcoRI insert containing the mini-Tn10Km element and the transposase gene of $IS10_R$ is located outside the inverted repeats of the mobile element and downstream of the pTac promoter. To obtain a transposon delivery plasmid with a host-independent regulation of its transposition, the EcoRI insert fragment is ligated to pBOR8, a derivative of pGP704 containing the lacIq gene from plasmid pMJR1560. This plasmid is unable to replicate in host strains devoid of the R6K-specified π protein product of the pir gene. pGP704 contains the conjugal transfer origin (oriT sequence) of the RP4 plasmid and can therefore be transferred to gram-negative bacteria when provided in trans with mobilization (Mob) functions. The MluI fragment internal to the inverted repeats containing the original-specified π protein product of the original kanamycin resistance gene of the mini-Tn10 is replaced by a fragment containing a SfiI-Ptt cassette, appropriately modified by the addition of the NotI site and MluI adapters, which produced the pLODPtt. This construction has unique SfiI, NotI, and XbaI cloning sites between the mini-Tn10 inverted repeats. The Ptt resistance marker (Pttr) of pLOFPtt is exchanged by kanamycin resistance to produce plasmid pLOFKm.

In view of the foregoing, a need exists for the construction of stable recombinant *Z. mobilis* strains which are capable of fermenting xylose and arabinose, or both, to ethanol through the generation of stable genomic inserts which encode the enzymes which are necessary for xylose and arabinose catabolism. The strains should be free of antibiotic resistance and stable for more than 40 generations in a non-selection media. It is also desirable for the strains to demonstrate a high specific rate of product formation at close to maximum theoretical product yield.

SUMMARY OF THE INVENTION

It is an object of the present invention to provide transposable element and plasmid vectors useful for the stable integration of foreign structural genes, encoding enzymes selected from the group consisting of xylAxylB, tal/tkt, and araBAD and at least one regulator gene for induction of the structural genes, into the *Z. mobilis* genome.

It is a further object of the invention to provide significantly different *Z. mobilis* strains capable of stable expression of the structural genes in a non-selection medium.

It is yet another object of the invention to provide significantly different *Z. mobilis* strains, having stable expression of the structural genes, but which are characterized by a high rate of specific product formation and conversion efficiency, when used as a bio-catalyst in a cellulose hydrolysate reaction mixture.

To overcome the problems associated with the related art and in accordance with the purpose of the invention, as embodied and broadly described herein, the present invention briefly includes: a transposon for stable insertion of foreign genes into a bacterial genome, including at least one operon having structural genes encoding enzymes selected from the group consisting of xylAxylB, araBAD and tal/tkt, and at least one promoter for expression of the structural genes in the bacterium, a pair of inverted insertion sequences, the operons contained inside the insertion sequences, and a transposase gene located outside of the insertion sequences; a plasmid shuttle vector for transformation of foreign genes into a bacterial genome, including: at least one operon having structural genes encoding enzymes selected from the group consisting of xylAxylB, araBAD and tal/tkt, at least one promoter for expression of the structural genes in the bacterium, and at least two DNA fragments having homology with a gene in the bacterial genome to be transformed.

The transposon and shuttle vectors are useful in constructing significantly different *Zymomonas mobilis* strains, according to the present invention, which are useful in the conversion of the cellulose derived pentose sugars into fuels and chemicals, using traditional fermentation technology, because they are stable for expression in a non-selection medium.

Additional advantages of the present invention will be set forth in part in the description that follows and in part will be obvious for that description or can be learned from practice of the invention. The advantages of the invention can be realized and obtained by the method particularly pointed out in the appended claims.

BRIEF DESCRIPTION OF THE DRAWINGS

The accompanying drawing, which are incorporated in and which constitute a part of the specification, illustrate at least one embodiment of the invention and, together with the description, explain the principles of the invention.

FIGS. 8A-8B are graphic representations which illustrates the stability of the stable xylose fermenting Z. mobilis strains C25 and D92 according to the present invention. The graph shows the stability of the plasmid-bearing and genomic integrated xylose-fermenting strains, using the ethanol process yield (8A) and xylose utilization parameters (8B) as indicators. Strains C25 and D92 of the present invention remained stable for more than 90 generations. The fermentation medium comprised RM with 1% glucose and 5% xylose and the temperature was constant at 30° C.

FIG. 13 represents a Southern analysis of the genomic integrated xylose/arabinose-fermenting Zymomonas strains from transposon integration using DIG-tnp and DIG-ara probes. G5,6,11,15,17,14 and 19 are araBAD integrants. C25 is the host control. Tn10G is the plasmid control. λH is a molecular weight marker: 23, 9.4, 6.6, 4.3, 2.3 and 2.0 kb.

FIGS. 17A-17B represent a bar graph results of the xylose (17A) and arabinose (17B) utilization of the genomic integrated xylose and arabinose-fermenting Zymomonas strains on RM containing 1% glucose, 2% xylose and 2% arabinose at 30° C. with pH control. These strains were inoculated form cultures at various generations on non-selective media.

DETAILED DESCRIPTION OF THE DRAWINGS

Figure 1:
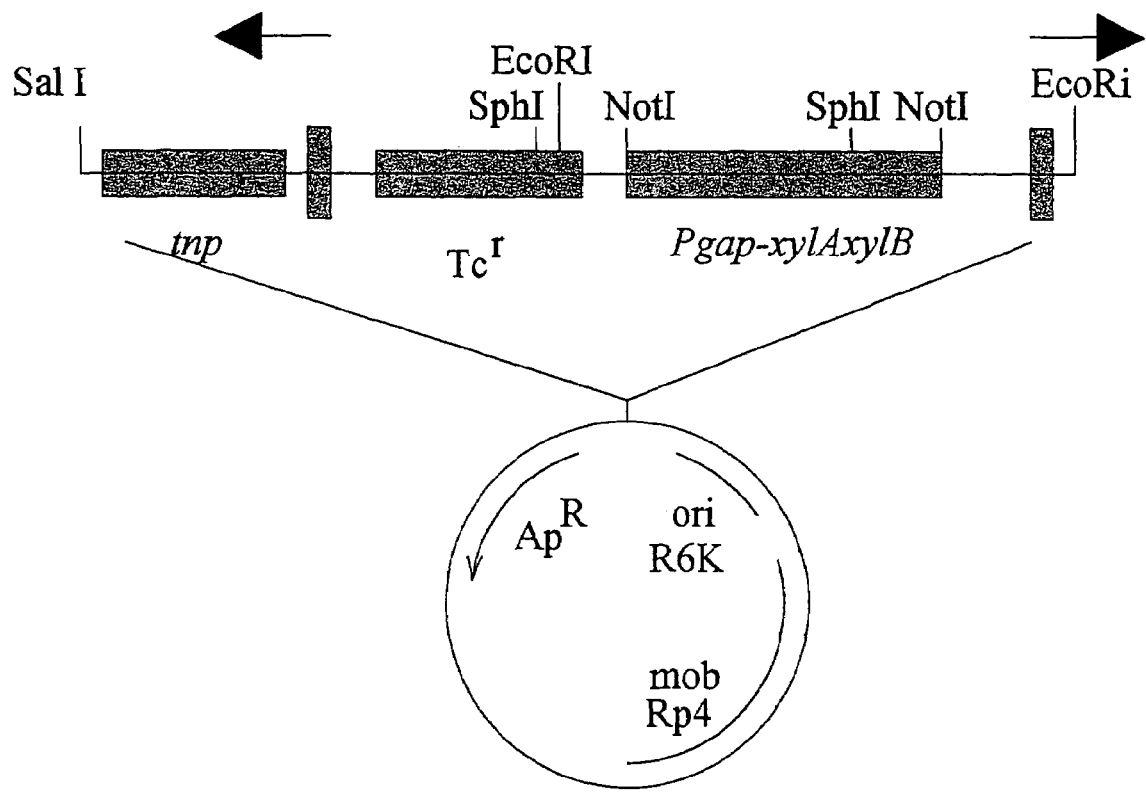
FIG. 1 is a plasmid map of Mini-Tn5 Tc in pGP704 containing the xylose assimilation operon according to the present invention.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All US patents are incorporated by reference as though fully set forth herein.

Reference now will be made in detail to the presently preferred embodiments of the invention, examples of which are illustrated in the accompanying drawings. For the examples described below, "plasmid-bearing strains" refers or relates to those strains and vectors described in the US patents identified in the Description of the Related Art. "*Z. mobilis* genome, or genomic" means the genes which, in toto, specify all the expressed and potentially expressible features associated with a given *Z. mobilis*. AX1 refers to *Zymomonas mobilis* Patent Deposit Designation PTA-1797; AX101 refers to *Zymomonas mobilis* Patent Deposit Designation PTA-4072; G8 refers to *Zymomonas mobilis* Patent Deposit Designation PTA-17961 mini-Tn5-tal/tkt-xylAxy/B refers to *Escherichia coli*: CC118 (mini tn5 xylAB-taltkt) Patent Deposit Designation PTA-1795; and the vector pZB 1862-ldhL-ara refers to *Escherichia coli*: DH5α (pZbl862-ldhL-ara) Patent Deposit Designation PTA-1798; and C25 refers to *Zymomomas mobilis* Patent Deposit Designation PTA-1799. All of the above are on deposit with the American Type Culture Collection, 10801 University Blvd., Manassas, Va. 20110-2209, received 2 May 2000, in accordance with the Budapest Treaty On The International Recognition Of The Deposit Of Microorganisms For The Purpose Of Patent Procedure and have been accepted.

EXAMPLES

Strains, Plasmids, and Media

*E. coli* bacterial strains CC118λ (pir), CC118λ (pir) (mini-tn5Tc), SM10λ (pir), and plasmids pUC19, pLOF/Km, pUC18sfi, pUT/Tc containing minitransposon Tn5, Tn 10 and pUC18Not were obtained from Dr. K. Timmis, GBF—Gesellschaft Fur Biotechnololgische Forschung mbH, Mascheroder weg 1 D—38124 Braunschweig, Federal Republic of Germany. *E. coli* DH5a was used as a host for the construction of the plasmids. *E. coli* SM10λ pir was used as donor strain in mating experiments. Strains of *Z. mobilis* ATCC 39676 and its derivative, 206C (U.S. Pat. No. 5,843,760) were used as recipients in accordance with the invention. Tn10-based plasmids were constructed and maintained in *E. coli* CC118.

*E. coli* strains were cultured in LB medium at 37° C. *Z. mobilis* strains were maintained anaerobically in RM (10 g/L yeast extract, 2 g/L KH$_2$PO$_4$) supplemented with 20 g/L glucose, D-xylose or L-arabinose, unless otherwise specified. All strains containing plasmids were grown in the presence of tetracycline (Tc) ((10 μg/ml in liquid *Z. mobilis*, and *E. coli* 20 μg/ml in agar for Z. mobilis; and 15 μg/ml in agar, or ampicillin (Ap), 100 μg/ml for *E. coli*)). For regeneration and selection of *Z. mobilis* transformants or transconjugates, mating plates ((10 g/L yeast extract, 5 g/L tryptone, 2.5 g/L (NH$_4$)$_2$SO$_4$, 0.2 g/L K$_2$HPO$_4$ and 50 g/L sugar)) supplemented with tetracycline or nalidixic acid (20 μg/ml) were used. All agar plates were made with 15 g/L agar.

Recombinant DNA Techniques

Plasmid DNA isolation, restriction endonuclease digestion, ligation and transformation, agarose electrophoresis and other recombinant DNA techniques were carried out in accordance with published protocols, Sambrook et al., (1989) *Molecular cloning: a laboratory manual*, Cold Spring Harbor laboratory press, Cold Spring Harbor, N.Y., or the respective reagent manufacture's instructions, were specified, and are well known in the art. Genomic DNA of *Z. mobilis* was extracted using three-milliliters of overnight cells resuspended in 250 ml of 50 mM Tris-50 mM EDTA buffer. The cells were treated with lysozyme at 37° C. for 30 min and 100 ml of 5% SDS solution and RNAase (final concentration equal to 20 ng/ml) were then added and the mixture was incubated for an additional 30 min. A phenol/chloroform extraction was performed twice, to remove the proteins. Genomic DNA was recovered by ethanol precipitation.

Conjugation and Transformation

Plasmids were transferred from the donor strains *E. coli* SM10λpir or S17-1 into *Z. mobilis* strains by conjugation with a filter mating technique (Conway et al., 1987). Plasmid DNAs were transformed into either *Z. mobilis* or *E. coli* cells by electroporation (Zhang et al., 1995)).

Southern Blot Analysis

DNA was transferred onto a nylon membrane using a Stratagene Posi Blot pressure blotter. DNA probes Tc, xylB, Tnp, and Tal were digoxigenin-UTP labeled by Polymerase Chain Reactions (PCR). The following primers were used for DNA labeling:

```
Tc:    5'-TTGCTAACGCAGTCAGGC-3'
       SEQ. ID NO. 1

5'-GAATCCGTTAGCGAGGTG-3'
       SEQ. ID NO. 2 xylB   5'-TATGGGTTCAGCGGCATGAG-3'
       SEQ. ID NO. 3

5'-ATGGGCATGAGATCCATAGCC-3'
       SEQ. ID NO. 4

Tnp    5'-TCCTAACATGGTAACGTTC-3'
       SEQ. ID NO. 5

5'-CCAACCTTACCAGAGGGC-3'
       SEQ. ID NO. 6

Tal:   5'-CGTCTAAAAGATTTTAAGAAAGGTTTCGATATGACGGACAA
       ATTGACC-3'
       SEQ. ID NO. 7

5'-CATTTTGACTCCAGATCTAGATTACAGCAGATCGCCGATC
       ATTTTTTCC-3'
       SEQ. ID NO. 8
```

Prehybridization and hybridization were performed according to established protocols described in the Boehringer Mannheim hybridization kit.

Example I

The following example illustrates the construction of Mini-TnSTc containing genes encoding the xylose assimilation enzymes and the conjugal transfer of this construct into *Z. mobilis* 206C and ATCC 39676. Mini-Tn5Tc containing genes encoding the xylose assimilation enzymes was constructed by inserting a Pgap-xylAxylB operon into the unique NotI site of Mini-Tn5Tc contained in plasmid pGP704. See FIG. 1. The Pgap-xylAxylB operons, were taken from plasmid pZB4 or pZB5, U.S. Pat. Nos. 5,712,133 and 5,726,053. The resulting plasmids, designated Mini-Tn5Tc xylA/xylB(X4) and Mini-Tn5Tc xylAxylB (X5), were transformed into the donor strain *E. coli* SM10λpir by electroporation and mated with either *Z. mobilis* ATCC 39676 and 206C strains. *Z. mobilis* 206C is disclosed in U.S. Pat. No. 5,843,760 which is incorporated herein by reference. Nine *Zymomonas* Tc$^r$ transconjugates were obtained from both SM10λpir donors containing Mini- Tn5TcxylAxylB (X4) and Mini-Tn5 TcxylAxylB (X5) by selection on media containing Tc and nalidixic acid. See, FIGS. 2(a), 2(b).

Genomic and plasmid DNA from the nine Z. mobilis Tc$^r$ transconjugates was then subjected to Southern blot analyses. Genomic and plasmid DNA from the transconjugates was digested with SphI, which cuts in the hybrid transposon and in the xylose operon, and the blots were then hybridized to either a Tc probe, a XylB probe, or a transposase Tnp probe. From the autoradiograph it was determined that: (1) the xylose operon Pgap-xylAxylB had been inserted into the Zymomonas genome, along with Tc$^r$ gene; (2) only a single insertion had occurred for each of the transconjugates; (3) the insertions were each at a distinct location in the genome; (4) the Tc$^r$ gene and XylB were not present the plasmid fraction; and (5) the tnp transposase gene was not present in transconjugates.

Enzymatic analysis of the Zymomonas Tc$^r$ Pgap-xyl-AxylB Transconjugates was made in order to confirm the expression of xylose isomerase (XI) and xylulokinase (XK) in the Zymomonas Tc$^r$ Pgap-xylAxylB transconjugates. This analysis revealed that the enzymatic levels of xylose isomerase for the all the transconjugates was about one-half that of their plasmid counterparts. Similarly, about one-half of the xylulokinase activities of the plasmid-bearing strains was observed in the integrants. Both XI and XK activities, expressed from a single copy of the genes, in the Zymomonas genome, were considerably higher than was expected, when compared to that of the 10 copies per cell found in a plasmid-bearing strains.

Example II (C25)

This example shows that to enhance the genetic stability of the recombinant Z. mobilis, in the absence of antibiotic selection, the xylose assimilation genes xylA and xylB, encoding xylose isomerase and xylulokinase, and pentose phosphate pathway genes, talB and tktA, encoding transaldolase and transketolase, were introduced into the Z. mobilis genome, using mini-Tn5. Two operons containing Pgap-xylA/xylB and Peno-talB/tktA were assembled in mini-Tn5 and the resulting plasmid was conjugated into Z. mobilis. With the help of the transposase located outside of the mini-Tn5 cassette, single copies of the Pgap-xylAxylB and Peno-talB/tktA were inserted into the Z. mobilis genome, as shown by Southern hybridization. Enzymatic analysis of xylose isomerase, xylulokinase, transaldolase and transaldolase indicated that all the genes were coordinately expressed and that the integrated strains produced about 30-70% of the enzymatic activities of the plasmid-bearing strains. These enzymatic levels were sufficient for the organism to grow and ferment xylose to ethanol.

Figure 3:
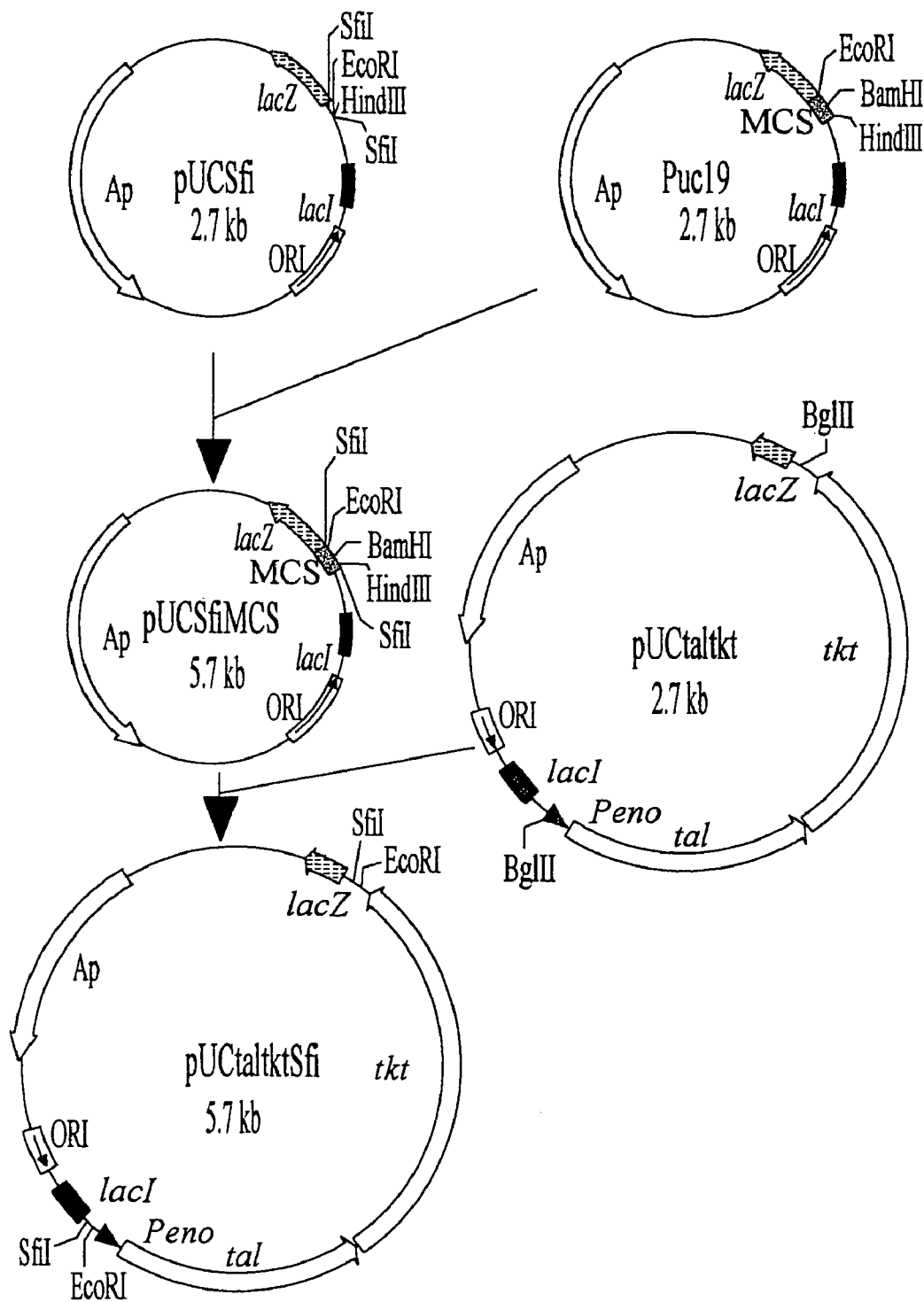
FIG. 3 is an illustration of the series of constructs resulting in the plasmid map of pUCtaltktSfi.

To facilitate the cloning process, the BglII fragment containing the operon Peno-talB/tktA was inserted into the BamHI site of a newly constructed auxiliary plasmid, pUS-CfiMCS as shown in FIG. 3. The auxiliary plasmid, pUS-CfiMCS, was constructed by inserting a EcoR I-Hind III fragment containing the multicloning sites from pUC19 into pUCSfi. PUCtaltkt was then constructed from pUCpfiMCS and pUCtaltktSfi, as shown in the Figure.

Figure 2:
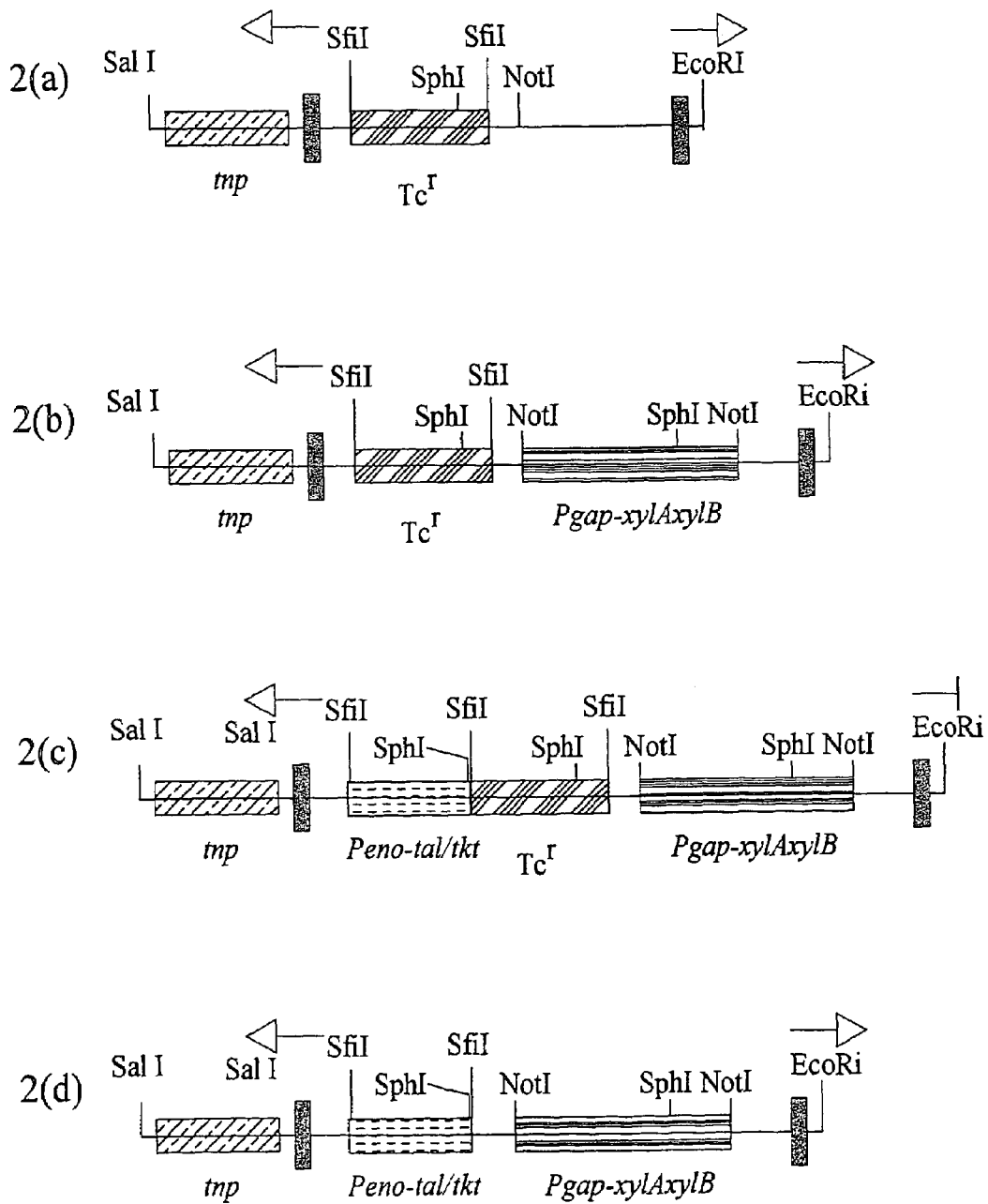
FIG. 2 is a series of plasmid maps illustrating the mini-Tn5 series constructs, according to the present invention.

Referring now to FIG. 2, the Peno-talB/tktA was then excised, from pUCtaltktSfi, as a SfiI fragment and was used to clone into mini-tn5-Tc-xylAXIB. As shown in the Figure, the Tcr gene is flanked by SfiI sites on the Tn5-Tc-xylAxylB cassette. Mini-tnS-Tc-xylAxylB was partially and completely digested with Sfi I and ligated to the Peno-talB/tktASfifragment, as shown in FIG. 2(c). The partial digestion yielded a plasmid containing the Tc$^r$ gene, designated as mini-tn5-Tc tal/tkt-xylAxylB ((FIG. 2(c)), while complete digestion yielded a plasmid, according to the invention herein, without the Tc$^r$ gene, designated as miniTnS-tal/tkt-xylAxylB. See FIG. 2(d).

Both plasmids were transformed into the donor strain E. coli, S17-1 and mated with Z. mobilis 206C. The resulting transconjugates were selected on mating media containing glucose, Tc, and nalidixic acid for miniTn5-tal/tkt-xyl-AxylB-Tc. For mini-tn5-tal/tkt-xylAxylB, the transconjugates were directly selected on mating media, containing xylose and nalidixic acid. A number of Tc$^r$ transconjugates (glucose-grown) were obtained for mini-tn5 tal/tkt-xyl-AxylB-Tc. Several xylose-grown transconjugates were obtained for mini-tn5-tal/tkt-xylAxylB.

Preliminary batch cultures were tested statically, at 30° C. without pH control in bottles with 80 ml RM containing 2% xylose for their fermentation dynamics. Colonies, taken from RM+2% xylose plates were cultured in an RM 2% xylose medium overnight at 20° C. until the culture had reached the stationary growth phase (optical density$_{600}$=0.1 at 500 nm), were used as the inoculum. Xylose and ethanol were analyzed using a Hewlett-Packard 1090L HPLC equipped with an HP 1047 A refractive index detector and a Biorad HPX-87H organic acid analysis column operating at 65° C., with a 0.01 N sulfuric acid mobile phase flow rate of 0.6 ml/min. The ethanol yield was calculated using either the weight of sugar fermented or the total available sugar in the medium. The maximum theoretical yield was based on 0.51 g ethanol/g xylose.

Figure 4:
FIG. 4 is the results of the Southern analysis tal/tkt—xylAxylB Z. mobilis transconjugates with Tal probe. C is the control plasmid mini Tn5 tal/tkt-xylAxylB. λH is the DNA size marker.
Figure 5:
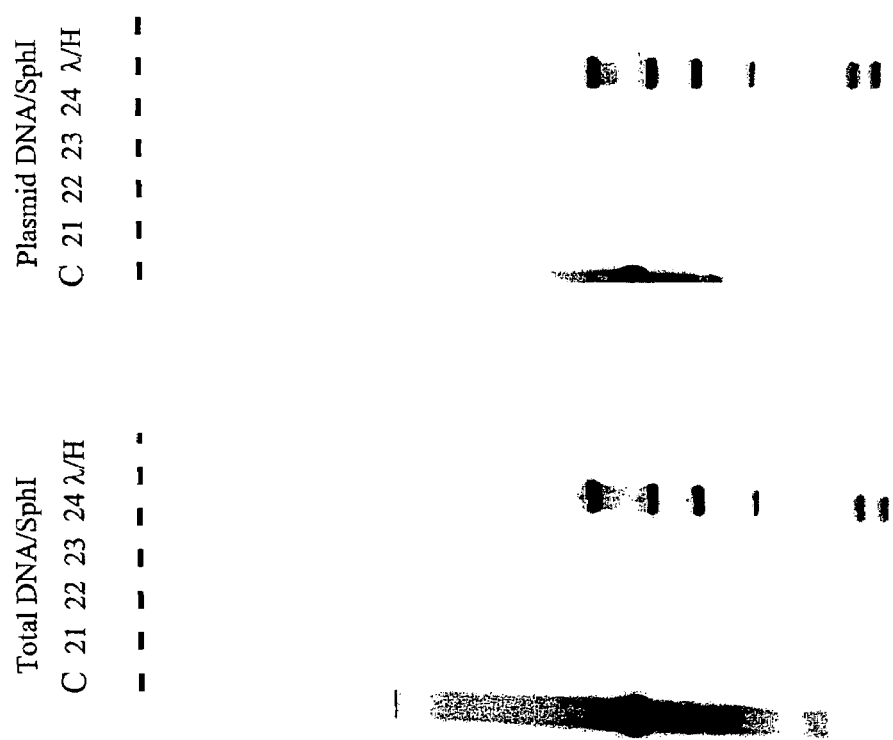
FIG. 5 is the results of the Southern analysis of tal/tkt-xylAxylB Z. mobilis transconjugates with Tnp probe. C is the control plasmid mini-TnS tal/tkt-xylAxylB. λH is the DNA size marker.

Southern blot analysis of genomic and plasmid DNA samples from the Z. mobilis transconjugates was made in order to investigate whether transposition of the mini-tn5 tal/tkt-xylAxylB cassette had occurred. Genomic and plasmid DNAs prepared from four transconjugates of mini-tn5 tal/tkt-xylAxylB were digested with SphI, which cuts twice within the cassette yielding one fragment with Tal probe homology. The blots were then hybridized to either Tal probe or Tnp probe The autoradiograph in FIG. 4 shows that one unique band greater than 4 kb (the size of Peno-talB/tktA), which is adjacent to Z. mobilis DNA, was detected from all the genomic DNA preparations when hybridized with Tal probe. Three of the samples (nos. 22,23, and 24 possibly siblings) also showed a band in the plasmid fraction, suggesting that the integration had occurred in the native plasmid. Clearly integration had occurred in the Z. mobilis genome for sample no. 21, and only one copy was inserted. Hybridization of genomic and plasmid DNA samples form these transconjugates with a Tnp probe (FIG. 5) revealed a lack of homology between the sample DNA's and Tnp probe. These results suggested that the xylose assimilation and pentose phosphate pathway genes, along with Tc$^r$ gene, had been transposed into the Z. mobilis genome, and that only a single insertion occurred in each of the transconjugates, and the insertions were at distinct locations in the genome.

Figure 6A:
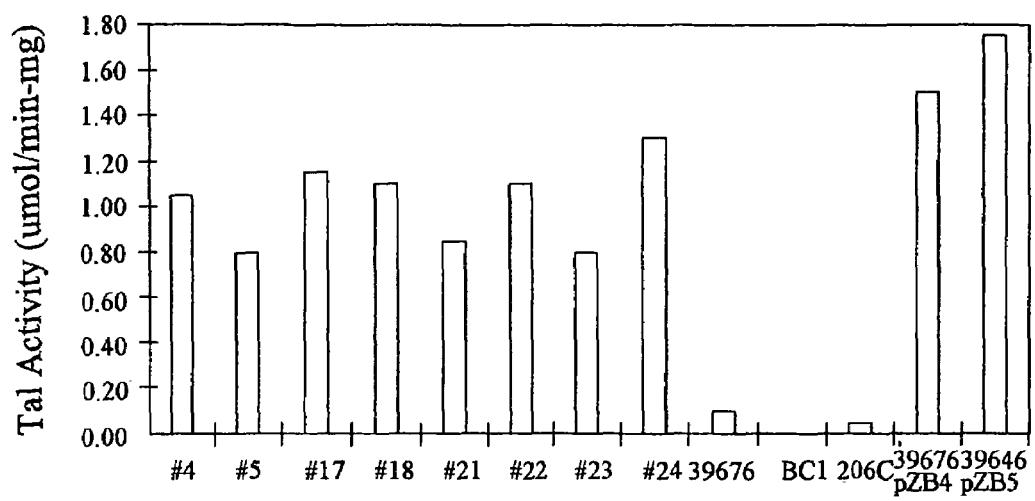
FIG. 6 is a graph of the enzymatic activities for several isolates of the stable xylose fermenting Z. mobilis strain according to the present-invention.
Figure 6B:
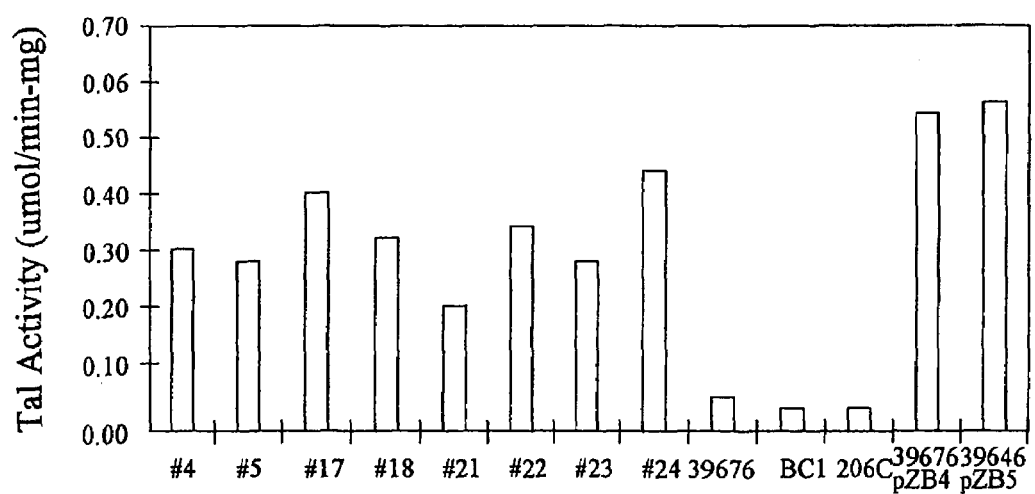

Xylose isomerase, xylulokinase, transaldolase and transketolase activities were measured as previously described in (Zhang et al., 1995), for the Z. mobilis transconjugates. As set forth above, it had been observed that expression of a single Pgap-xylAxylB copy on the genome was about one-half that of the XI and XK enzymatic yielded for the plasmids-bearing strains. However, when enzymatic analysis was done to confirm whether transaldolase (TAL) and transketolase (TKT) had been expressed in the Zymomonas tal/tkt-xylAxylB-Tc and tal/tkt-xylAxylB transconjugates, as shown in FIG. 6, it was revealed that the enzymatic levels of TAL, for the all the transconjugates (nos. 4,5,17,18,21,23, and 24), was about 50-70% that of their plasmid counterparts. About 30-70% of the TKT activities of the plasmid-bearing strains was observed in the integrants. While the plasmid integrants had slightly elevated TAL and TKT activities, both TAL and TKT activities, expressed from a single copy of the genes in the *Zymomonas* genome, were considerably higher than was expected when compared to that of the copies per cell found on a plasmid- bearing strain.

Figure 7:
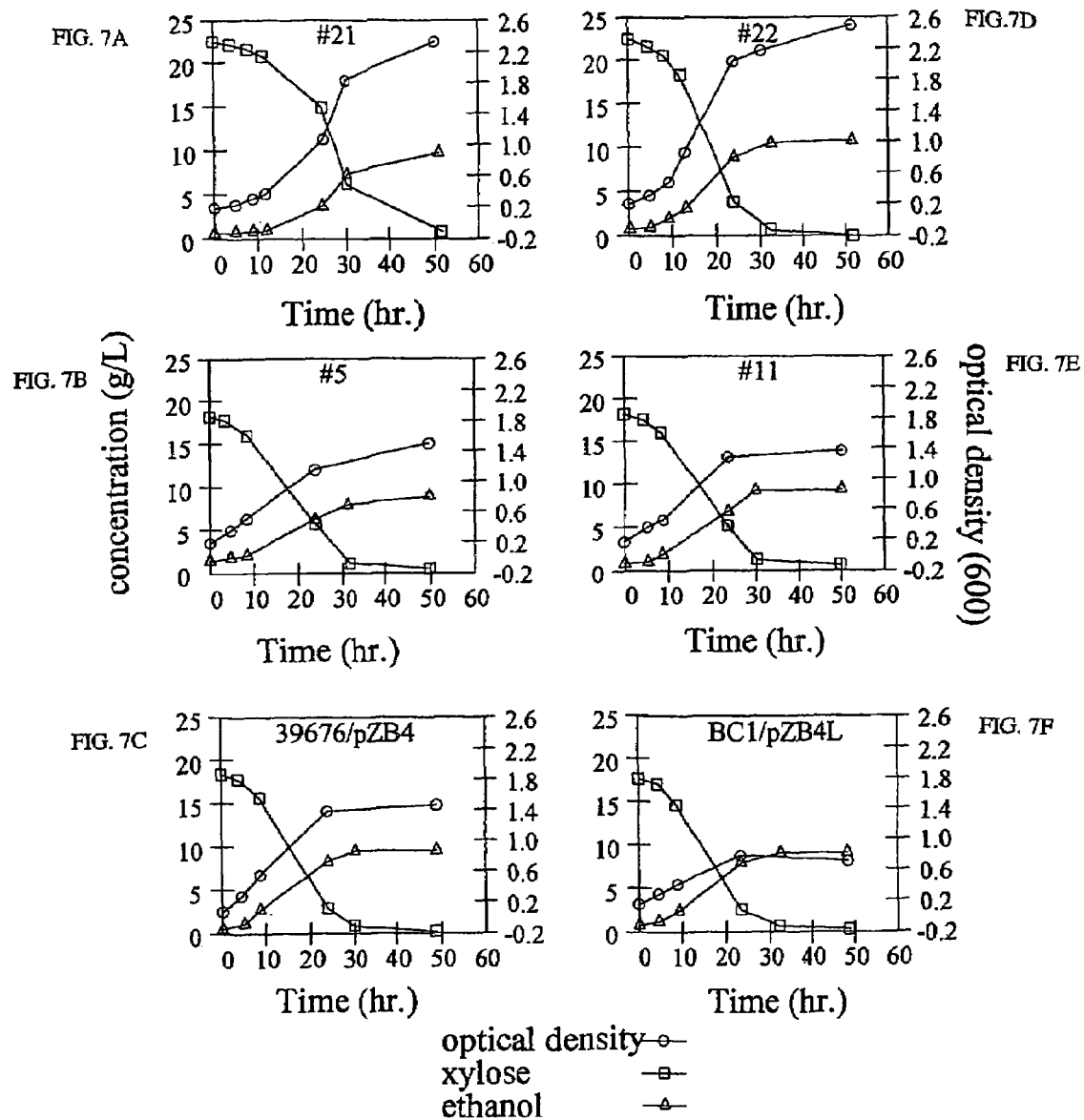
FIGS. 7A-7F are graphs of the fermentation profiles for four of the isolates (nos. 21: (7A), 22 (7D) 5 (7B) and 11 (7E)) of FIG. 6 and their performance in relation to the plasmid bearing strains 39673/pZB4 (7C) and BC1/pZB4L (7F).
Figure 9:
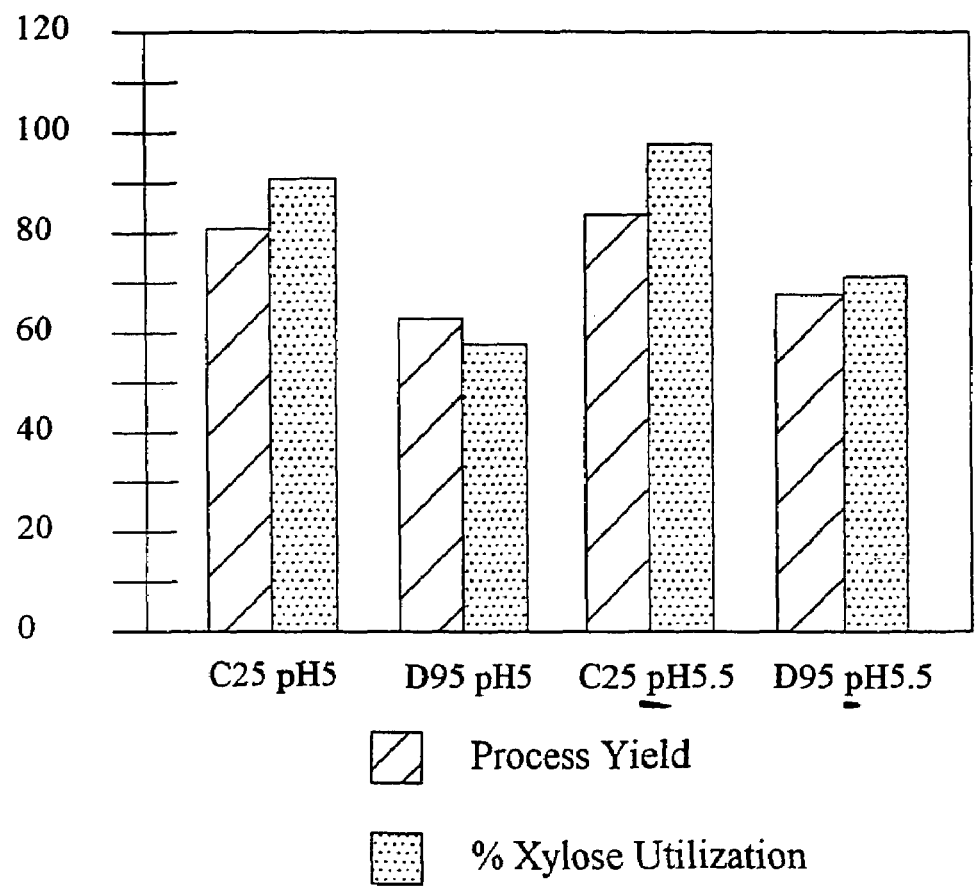
FIG. 9 illustrates the biomass concentration at optical density ($OD_{600}$), the xylose utilization as a function of time, ethanol production as a function of time, and process yield compared to the percent of xylose utilization for batch fermentations of the genomic integrated xylose-fermenting strains, C25 and D92, in a RM medium containing 4.5% glucose, and 4.5% xylose at pH 5.0 and pH 5.5 at 30° C., according to the present invention.

All four of the tal/tkt-xylAxylB *Zymomonas* integrants (nos. 21, 22, 5, and 11) were able to grow on xylose. Preliminary fermentation studies for these integrants was then made using a 2% xylose substrate, at 30° C. The fermentation profiles, for these integrants, is shown in FIG. 7, In the Figure, the growth and sugar utilization rates of *Z. mobilis* integrant no, 21 was slower than that of the plasmid bearing strain 39676/pZB4. However, most of the *Z. mobilis* integrants (nos. 22,5, and 11) were comparable to the plasmid-bearing strains. All the integrants produced ethanol from xylose, at 92% of the maximum theoretical product yield.

Stability of these genomic integrated strains and three plasmid bearing strains was measured in a non-selective medium. All strains were cultured in an RMG medium, and serially transferred about every 10 generations daily. At every 40 generations, the cells were used to inoculate a flask of RM media containing 1% glucose, and 5% xylose in order to measure their ability to ferment xylose to ethanol. Ethanol process yields and xylose utilization rates were used as the milestones for stability. Two of the genomic integrated strains demonstrated stability for more than 90 (C25 and D92 generations, while the plasmid-bearing strains (206/pZB4, 206/pZB4L and BClpZB4L) were stable for about 40 generations. See, FIG. 8.

The fermentation performance of strains C25 and D95 was analyzed in an RM medium containing a different concentrations of total glucose and xylose (1% glucose and 5% xylose; 3% glucose and 3% xylose; and 4.5% glucose and 4.5% xylose) under pH controlled conditions. As shown in the Figure, strain C25 demonstrated much better xylose utilization and ethanol process yields at both pH 5, and pH 5.5 in RM containing 4.5% glucose and 4.5% xylose than D95. Consequently, in the subsequent examples the three arabinose assimilating genes (araBAD) were integrated into the C25 genome.

Example III (AX)

The following example demonstrates the introduction of the arabinose assimilation enzymes in the genome of C25 through homologous recombination via ldh and transposition using mini-transposon Tn10. Plasmid pZB1862-ldhL-ara, described below, was used to transform *Z. mobilis* or *E. coli* by electroporation. Transformants were selected on mating plates supplemented with glucose and tetracycline. Tcr colonies were further confirmed to be Ara$^+$Xyl$^+$ by growth on RM supplemented with xylose or arabinose (RMS and RMA). Plasmid Tn10G, also described below, was transferred from an *E. coli* SM10λpir donor to *Z. mobilis* C25 by conjugation with a filter mating technique (Conway et al., 1987). The resulting transconjugates were selected on mating plates containing arabinose.

A. Construction of pZB1862-ldhL-ara and integration in C25 using homologous recombination Previous attempts to integrate araBAD in the *Zymomonas* genome, using a 1-kb ldh fragment as the homologous region, did not succeed. In order to increase the recombination frequency, a larger homology region was used. A 2.5-kb DNA fragment, which includes ldh and the flanking region was amplified using Pfu PCR. The primers were designed based on the DNA sequence of *Z. mobilis* CP4, published in Yamano I., (1993) *Journal of Bacteriology*, Vol. 175, 3926-3933. Although a 2.5-kb fragment was expected from PCR, according to the published sequence, a 3.4-kb fragment was obtained instead. After digesting the 3.4-kb fragment with BamFl, two fragments (2.5 and 0.9 kb) were obtained. Both fragments were tested by PCR, using primers designed to anneal to only the ldh. The 2.5-kb fragment produced a PCR product of the correct size, whereas the 0.9-kb fragment did not, indicating that the former contained the ldh sequence. Therefore, the 2.5-kb BamHI fragment (designated ldhL) was cloned and used as the homologous region for gene integration into C25.

The ldhL fragment and digoxygenin (DIG)-labeled ldh, ara, and tnp probes were amplified by PCR using either Pfu (Stratagene, La Jolla, Calif.) or Taq DNA polymerase (Qiagen, Valencia, Calif.). DIG-TJTP was purchased from Boehringer Mannheim, Indianapolis, Ind. A I probe was used to probe for IS10$_R$, the transposase gene of Tn10. PCR products for ldhL, ldh, ara, and tnp are 2.5, 1, 1.4 and 0.8 kb, respectively. The following primer sequences were used:

```
2 ldhL:   5'-TCGCGGATCCTCTATCCCTTTATTTTTCTATCCCCATCACCTCGG-3'
          SEQ. ID NO. 9

5'-TCGCGGATCCGCGGCTGACATACATCTTGCGAATATAGGG-3'
          SEQ. ID NO. 10

DIG-ldh:  5'-TCGCGGATCCGTCTATGCGCGTCGCAATATTCAGTTCC-3'
          SEQ. ID NO. 11

5'-TCGCGGATCCGTCGCTTGTCTATTAAACAAGCGCATCCGGC-3'
          SEQ. ID NO. 12

DIG-ara:  5'-CTAACATGTTGACTCCTTCTCTAGACTTAGCG-3'
          SEQ. ID NO. 13

5'-GTTGAAACCGCTGGGCACCACGC-3'
          SEQ. ID NO. 14

DIG-tnp:  5'-CGCACTACACGGTCGTTCTGTTAC-3'
          SEQ. ID NO. 15

5'-GGTTGCAGCCACGAGTAAGTCT-TC-3'
          SEQ. ID NO. 16
```

Figure 10:
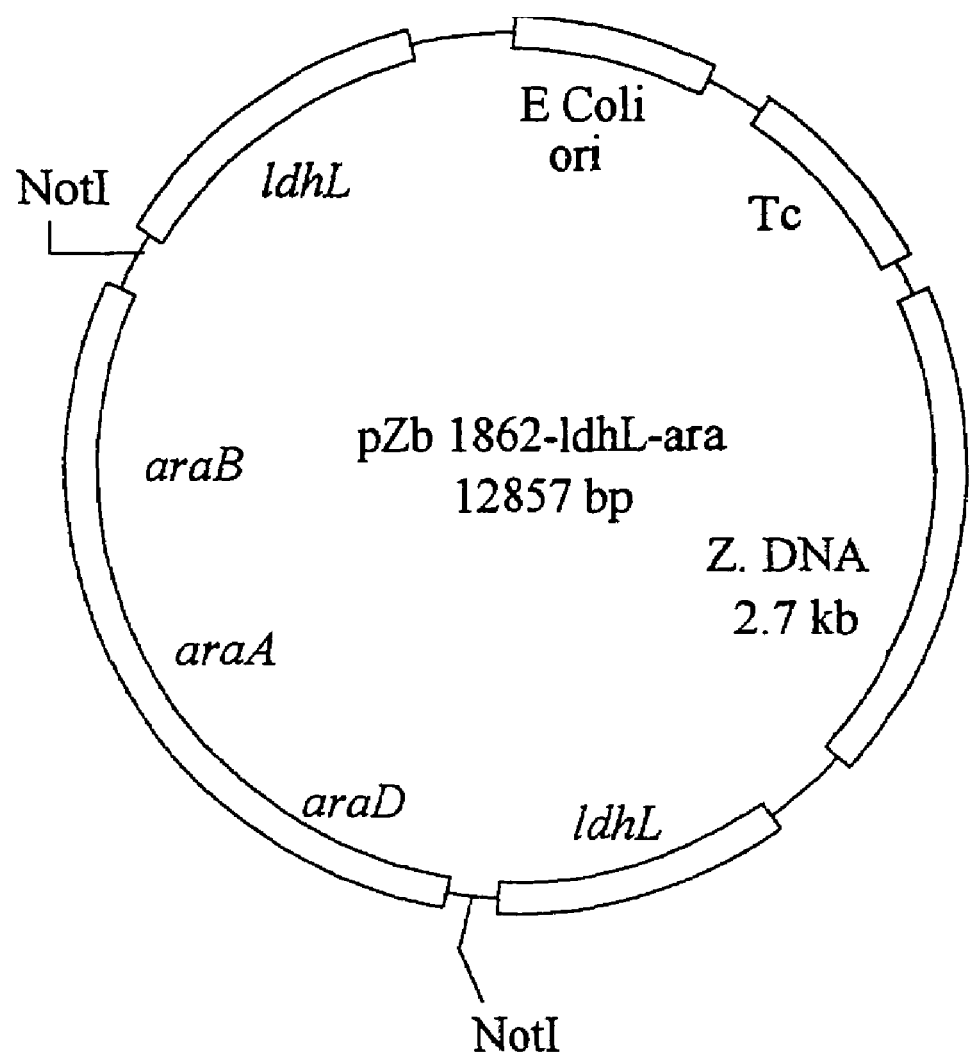
FIG. 10 is a map of the integrative plasmid pZB 1862-ldhL-ara. The araBAD is inserted in the NotI site of ldhL disrupting ldh. The construction is based on the replicative plasmid pZB 1862 of Z. mobilis.

For cloning purposes, a Not I site was introduced in ldhL by insertion of an oligonucleotide 5'-CATGCGCGGC-CGCC-3' at NcoI site, which is located in the middle of the ldh gene. The new NotI site was approximately 1.4 and 1.1 kb from either end of ldhL. A BamHI fragment of ldhL (2.5 kb) containing the NotI site was ligated into pZB1862 at a BcII site. Finally, a 4.4-kb Pgap-araBAD, isolated from pZB206 (U.S. Pat. Nos. 5,712,133 and 5,726,053), was cloned into the NotI site, of ldhL, to form the integrative plasmid, pZB1862-ldhL-ara. See, FIG. 10.

The Pgap-araBAD operon, containing the three arabinose-assimilating genes, was integrated into the ldh site in the C25 genome through homologous recombination. To integrate the araBAD genes into the genome of C25, pZB1862-ldhL-ara was constructed in *E. coli* DH5a. The plasmid pZB1862-ldhL-ara was transferred into C25 by electroporation. The Tc resistant transformants were selected and tested for growth on arabinose. During propagation of the transformants, Pgap-ara-BAD could be integrated in the genome of C25 by the replacement of ldhL with the ldhL'-araBAD-ldhL' cassette (from the plasmid) through homologous recombination.

To enrich and isolate the integrants, plasmid curing was conducted for the transformants. Plasmid pZB1862-ldhL-ara will replicate in *Z. mobilis*. However, *Z. mobilis* tends to lose foreign plasmids at sub-optimal growth conditions (e.g. 37° C.). Using this characteristic, curing of pZB1862-ldhL-ara was achieved by subculturing C25 transformants at 37° C. in the absence of Tc for several transfers. Cultures form each transfer were constantly monitored of for the loss of the plasmid. By the third transfer, 100% of the cells became $Tc^s$, indicating a loss of the plasmid. Cultures from the $3^{rd}$, $4^{th}$, $5^{th}$, and $6^{th}$ transfers were inoculated in RM containing arabinose (RMA), at 30° C., to enrich the growth of potential Pgap-araBAD integrants. The enriched cells were transferred to RMG plates and replica-picked onto RMA, RMX, and RMGTc plates. Several integrants (AX) with the phenotype of $Xyl^+Ara^+Tc$ were subjected to further analysis, as described below. These integrants were able to use either xylose or arabinose as a sole carbon source.

B. Construction of Tn10G and Conjugation into C25

Figure 11:
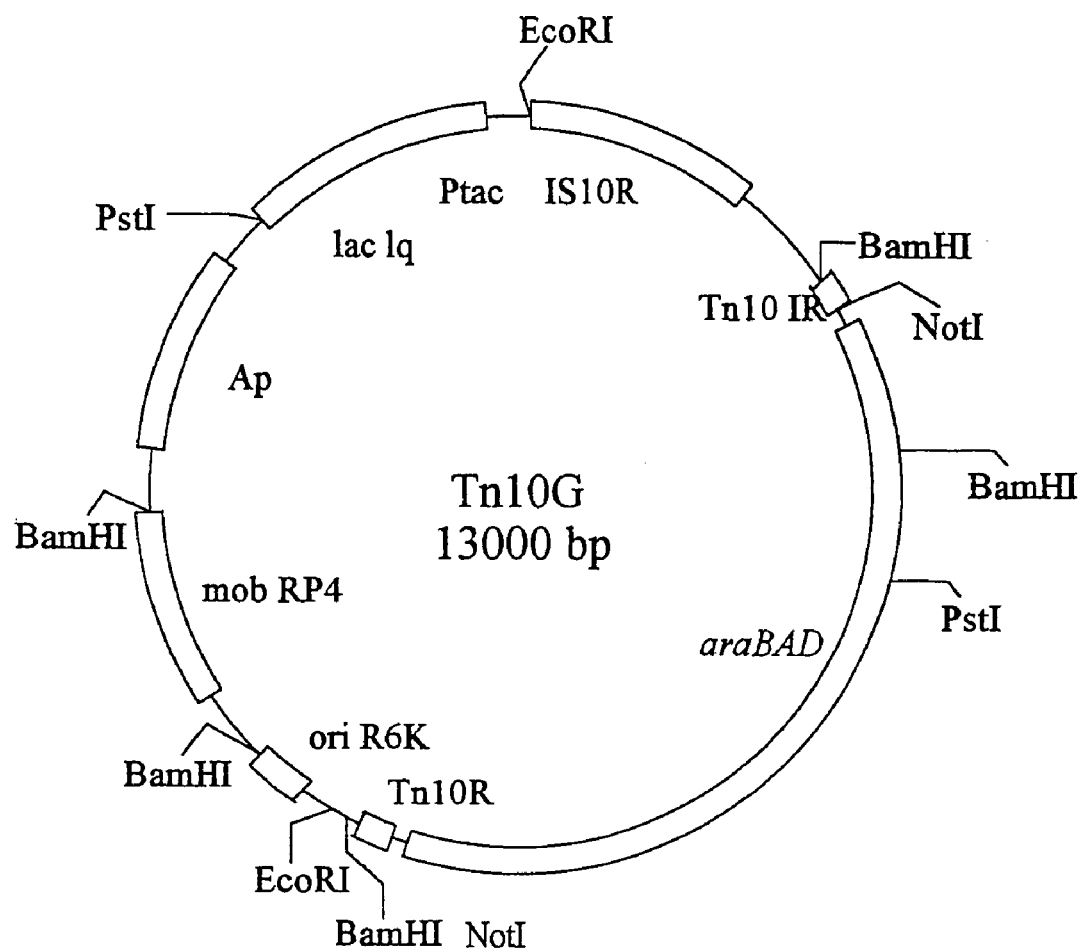
FIG. 11 is the plasmid map of Tn10G. $IS10_R$ is the transposase gene. IR is the inverted repeat sequence of the transposon. AraBAD was inserted between the two inverted repeats at the NotI sites.

Mini-Tn5 was used for constructing C25 with Peno-tal/tkt and Pgap-xylAB operons. Although the transposase gene did not exist in C25, mini-Tn10 was used for the subsequent integration of Pgap-araBAD to avoid any possible incompatibility between the same transposons. Plasmid Tn10G (FIG. 11) was constructed based on the Tn-10-based delivery plasmid, pLOFKm. The Kmr gene was replaced by a NotI fragment of Pgap-araBAD, isolated from pZB206. Tn-10G was constructed and maintained in *E. coli* C118. The plasmid was then transferred into the mating donor, *E. coli* SM10λpir for conjugation with *Z. mobilis*. Since Tn-10G is a suicide plasmid in *Z. mobilis*, only transconjugates with araBAD integration were able to grow on mating plates, supplemented with arabinose. The *E. coli* SM10λpir donor was inhibited, in the plates, by the presence of nalidixic acid. Transconjugates appeared on mating/ara plates in 7 days. Colonies were replica-picked onto RMA and RMX to confirm their phenotypes. Eighty-six percent of the colonies picked were $Xyl^+Ara^+$. Twenty colonies from the pick-plates were cross-transferred to different plates (from xylose plates to arabinose plates or vice versa). Sixty percent of those colonies remained $Xyl^+Ara^+$. Twenty colonies were analyzed in a preliminary Southern hybridization (data not shown). Using the tnp probe, about 50% of the strains contained the transposase gene in the genome. Eight integrants were then subjected to detained analysis by Southern hybridization.

Figure 12A:
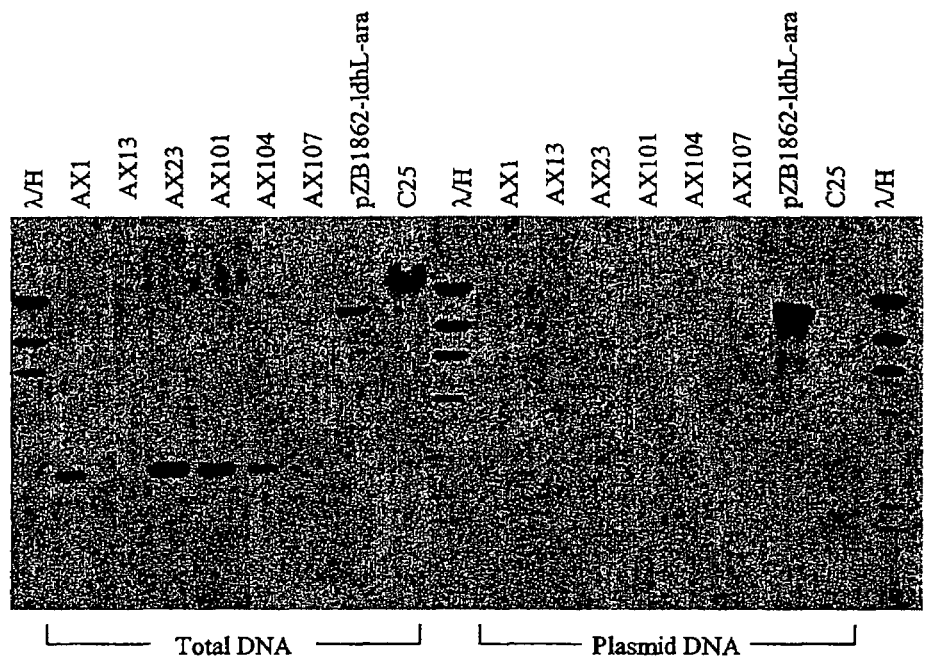
FIG. 12 shows the Southern analysis of the genomic integrated xylose/arabinose-fermenting Z. mobilis strains from homologous recombination using DIG-ara and DIG-ldh probes. AX1, 13, 23, 101, 104, and 107 are araBAD integrants. C25 is the host control. pZB1862-ldhL-ara is a plasmid control isolated form DH5α. λ/H is a molecular weight marker: 23, 9.4, 6.64.3, 2.3 and 2.0 kb.
Figure 12B:
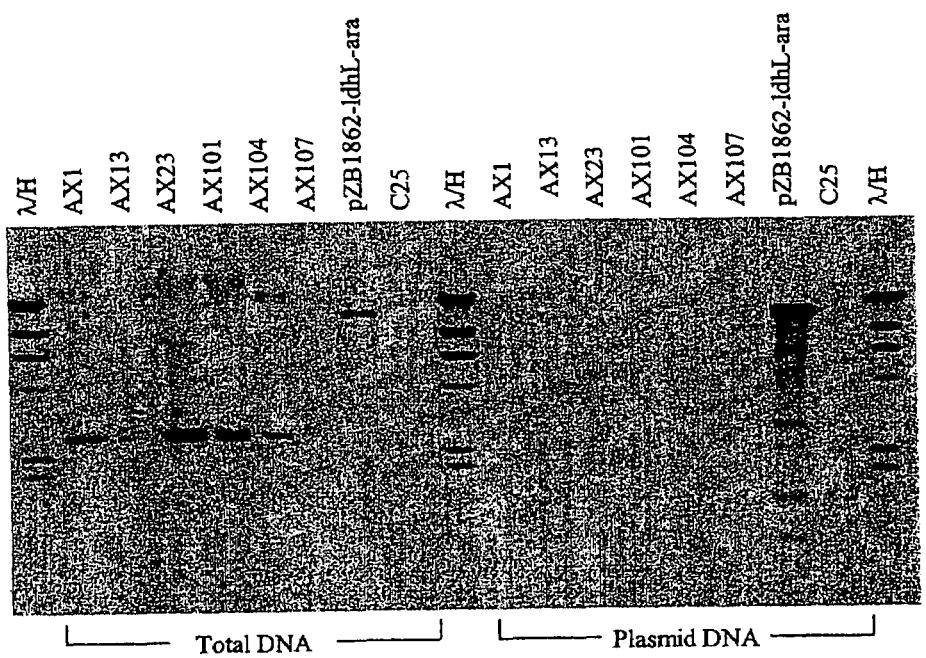

Integration of Pgap-araBAD in ldh of C25 was confirmed by Southern hybridization, for the pZB1862-ldhL-ara integrants DNA using the DIG-labeled ara and ldh probes See, FIGS. 12(a) and (b). There is only one PstI site on pZB1862-ldhL-ara and it is located in Pgap-araBAD. Therefore, one hybridizaion band (12.9 kb) from the PstI-digested plasmid was expected, using the ara probe. With Pgap-araBAD integrated in the genome two bands generated by the PstI site in Pgap-araBAD and the adjunct PstI sites on the genome located outside the Pgap-araBAD were expected. The results from FIG. 13(a) clearly showed that two bands form the total DNA preparation hybridized with the ara probe and demonstrated integration of Pgap-araBAD. The lack of hybridization bands form plasmid DNA of integrants indicated that integration had occurred on the genome, rather than on native plasmids. To shown that the ldh was disrupted by the Pgap-araBAD integration, the same DNA was transferred and hybridized with the ldh probe. As expected, the hybridization patterns for the integrants were exactly the same on both blots, except for C25, as shown in FIG. 12 (b). The total DNA from the host strain, C25, used for Pgap-araBAD integration, which has an intact ldh, showed only one band. The results confirmed that araBAD was integrated in ldh of C25.

Figure 13A:
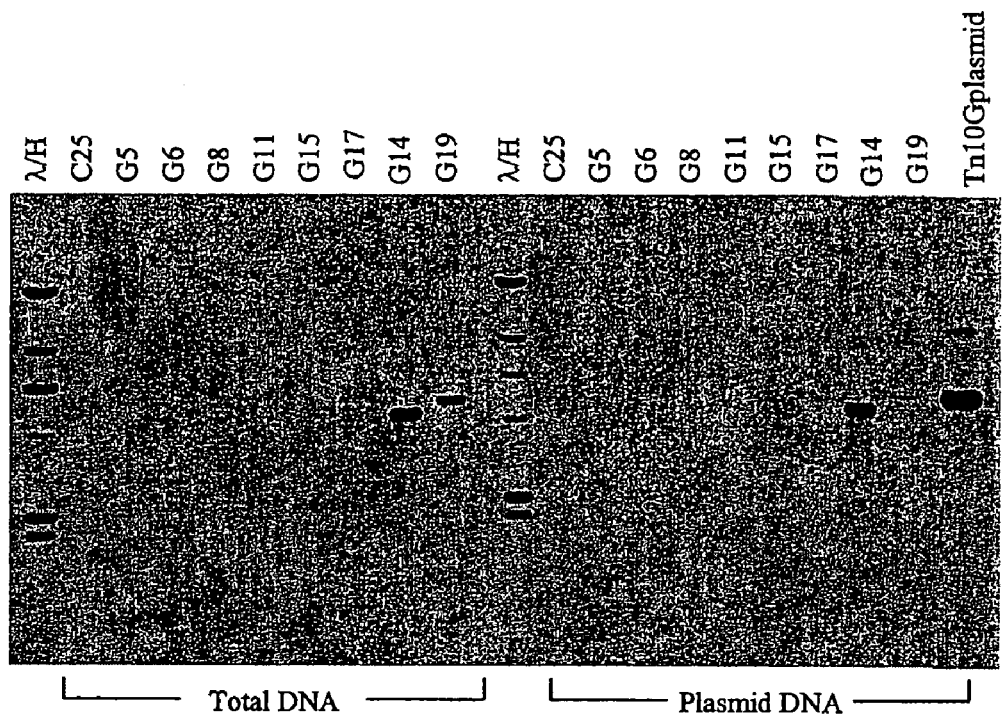
FIG. 13(a) is the tnp PstI digestion and FIG. 13(b) is the probe are PstI digestion.
Figure 13B:
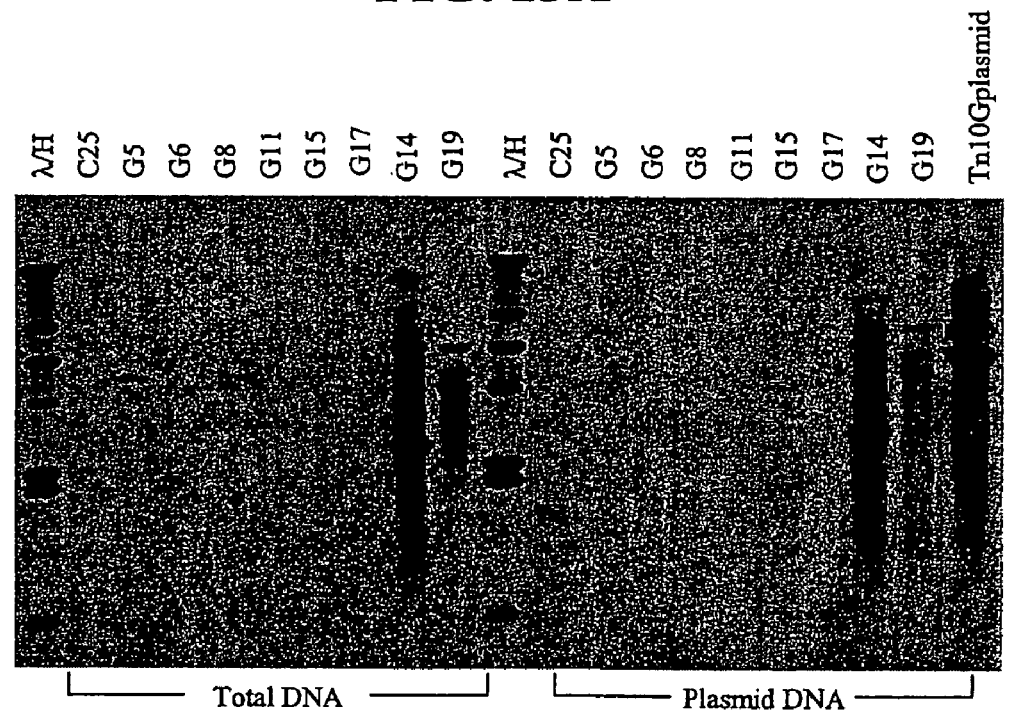
Figure 14A:
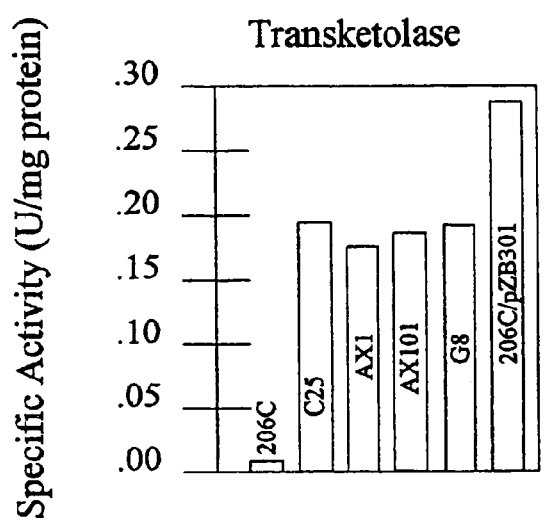
FIGS. 14A-14D representbar graphs of the enzymatic activities of the transketolase (14A), transaldolase (14B), xylose isomerase (14C) and xylulokinase (14D) of the genomic integrates strains. 206C/pZB301 is a plasmid control. 206C is a host control. C25 is the xylose-fermenting integrant. G8 is the xylose/arabinose fermenting integrant from Tn10 transposition. AX1 and AX101 are the xylose/arabinose fermenting integrants from homologous recombination.
Figure 14B:
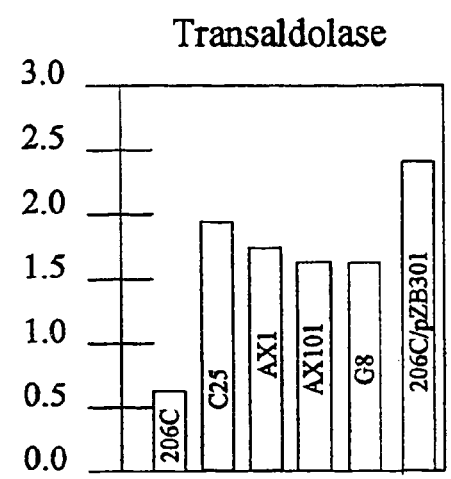
Figure 14C:
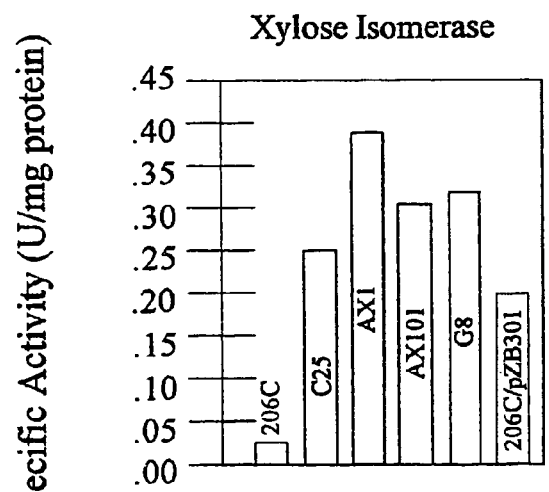
Figure 14D:
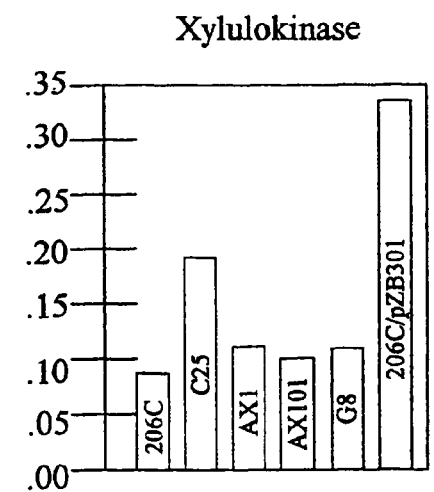

FIGS. 13(a) and (b) show the Southern hybridization results using DIG-labeled Tnp and ara probes, respectively, for the for the eight Pgap-araBAD transposon integrants generated by Tn-10transposition. DNA was digested with a PstI restriction enzyme. PstI cuts Tn10G into two fragments (7.7 and 5.9 kb) and only the 5.9-kb fragment carries the transposase gene (ISIOR). Both fragments hybridized with an ara probe. According to the blots, only G8, G11, G15 and GH17 were ara-positive and tnp-negative. Different band patterns indicated that Pgap-araBAD was integrated at different loci in the genome. Although the transposase gene was not expected to remain in the genome of the integrants, four strains (G5, G6, G14 and G19), out of the eight, contained the transposase gene. Furthermore, G14, and G19 contained the transposase gene on the plasmid. With an ara probe, two bands from the integrants were expected. However, only single bands were observed. To solve this ambiguity, PCR was conducted, for the integrants, using ara primers and it was confirmed that all eight integrants contained Pgap-araBAD in the genome (data not shown).

Xylose isomerase (X1), xylulokinase (XK), L-arabinose isomerase (L-AI), L-ribulokinase (L-RK), L-ribulose-5-P-4-epimerase (L-Repi), transketolase(TKT) and transaldolase (TAL) were assayed, using cell-free extracts of the *Z. mobilis* integrants and control strains, according to Zhang, et al., 1995; and Deanda et al., 1996, with minor modifications. Cell-free extracts were prepared by collecting the cultures at late-log phase (30° C., $OD_{600}$ approximately 1.2), washing once with sonication buffer (10 mM Tris-HCl, pH 7.6 10 mM $MgCl_2$) and sonicating. The cell debris was removed by centrifugation (14,000 rpm, 45 min 4° C.). In the L-AI assay, the volumes of timed samples were scaled down by half (50 µl), 70% $H_2SO_4$ (1.5 ml) and 0.12% carbazole (50µ). All of the tubes were maintained in a 25° C. water bath, both before and after the addition of 70% $H_2SO_4$, until reading the absorbency. The samples were taken at 0,5,10, and 20 min during the reaction.

Figure 15:
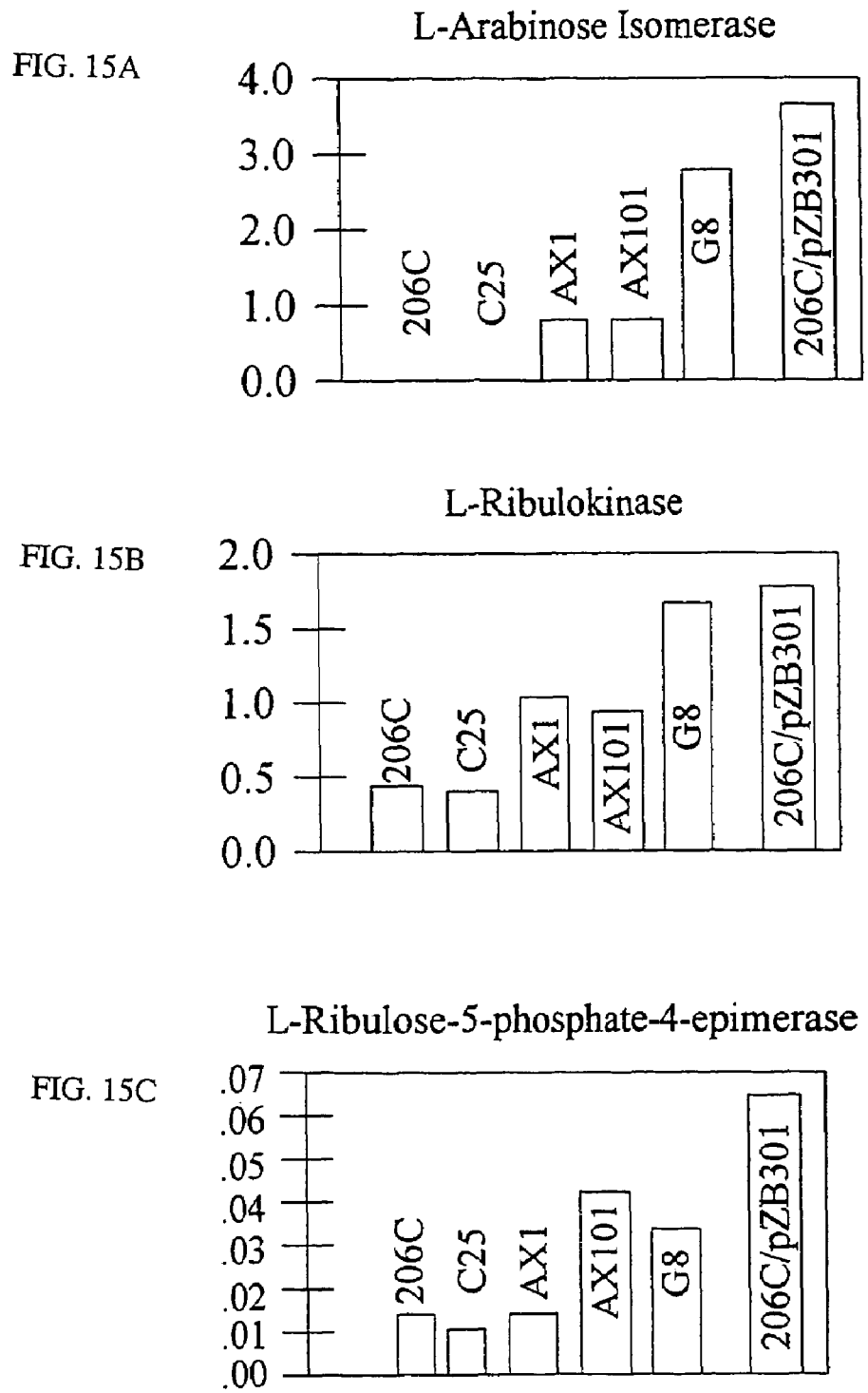
FIG. 15A-15C represent bar graph results of the enzymatic activities of L-arabinose isomerase (1SA), L-ribulokinase (1SB) and L-ribulose-5-phosphate-4 epimerase (15S) of genomic integrated strains. 206C/pZB301 is a plasmid control. 206C is a host control. C25 is the xylose-fermenting integrant. G8 is the xylose/arabinose-fermenting integrant form Tn10 transposition. AX1 and AX101 are the xylose/arabinose-fermenting integrants from homologous recombination.

Although the integrants, from both homologous recombination and transposon integration, were able to grow on D-xylose and L-arabinose, the expression level of the integrated genes it was determined by measuring enzymatic activity. Isolates C25/AX1, C25/AX101, and C25/G8 were chosen for the enzymatic assays because they were the most stable integrants, as determined in the stability studies described below. The results of the enzymatic assays are summarized in FIGS. 14 and 15. For all assays (with and exception of xylulokinase), integrants showed positive activities as compared to the controls (C25 and/or 206C). It is believed, at this moment, that the low activity of XK for the integrants, might be due to experimental error, the nature of the assay, or both. In most assays, (excluding L-ribulokinase and xylose isomerase), the integrants showed lower activities than the plasmid-bearing strain (206C/pZB301). This is presumable related to the copy number of the genes.

For stability studies, the cultures were inoculated into test tubes containing RMG, incubated overnight at 30° C., and transferred daily to RMG tubes. The inoculum was controlled to allow transfer every 10 generations. At every 40 generations, the cells were used to inoculate flasks, containing a mixture of sugars, to test the fermentation capabilities on the sugars without pH control at 30° C. Batch fermentation studies were performed at 30° C. with pH control in Bio-StatQ chemostats, a trademark of B, Braun, Allentown, Pa., using 500 ml as the working volume. The pH was automatically controlled with 2N KOH. Initial sugar concentration and pH varied between each batch, depending on the culture conditions. All the sugars used were reagent grade. Samples were taken periodically throughout the fermentation, and analyzed for sugars, ethanol and by-products with HPLC, as described previously (Zhang 1995). Optical density, at 600 nm (OD600), was measured in order to monitor cell growth. Ethanol yield was based on the amount of total available sugar.

Figure 16:
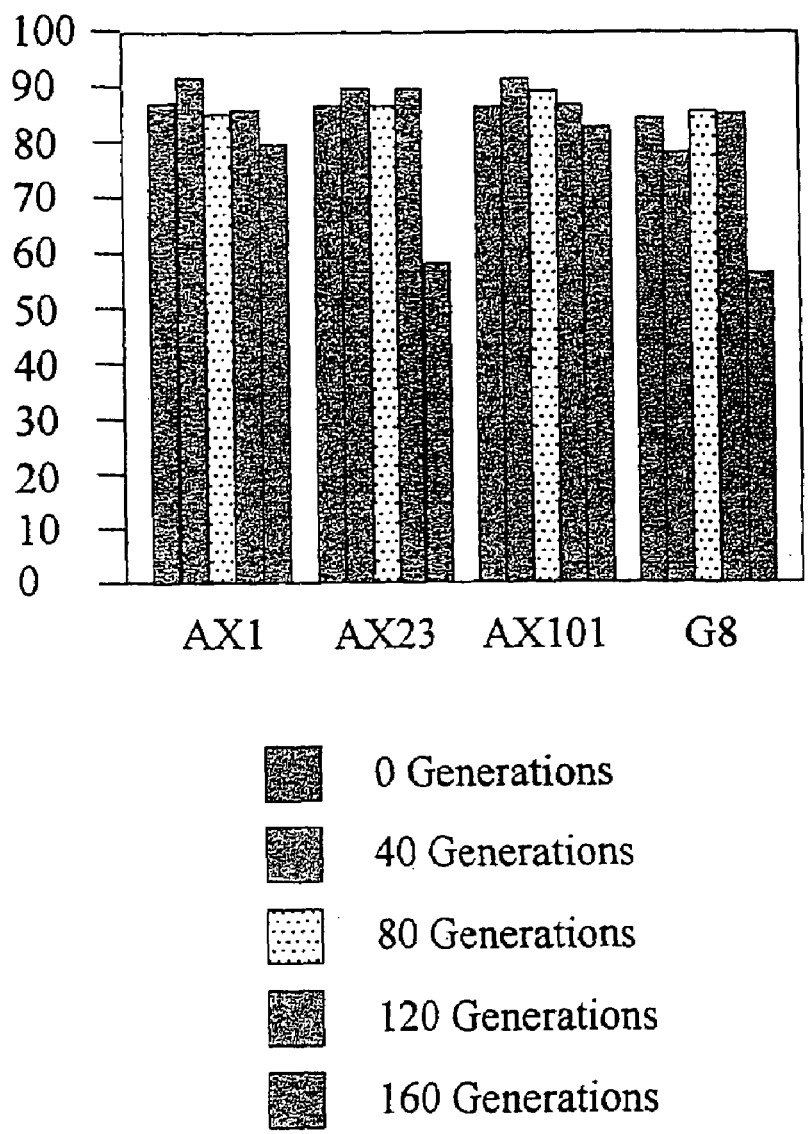
FIG. 16 represents a bar graph result of the ethanol process yields of the genomic integrated xylose and arabinose-fermenting Zymomonas strains on RMGXA (1:2:2%) at T=30° C., without pH control. These strains were inoculated form cultures at various generations on non-selective media.
Figure 18:
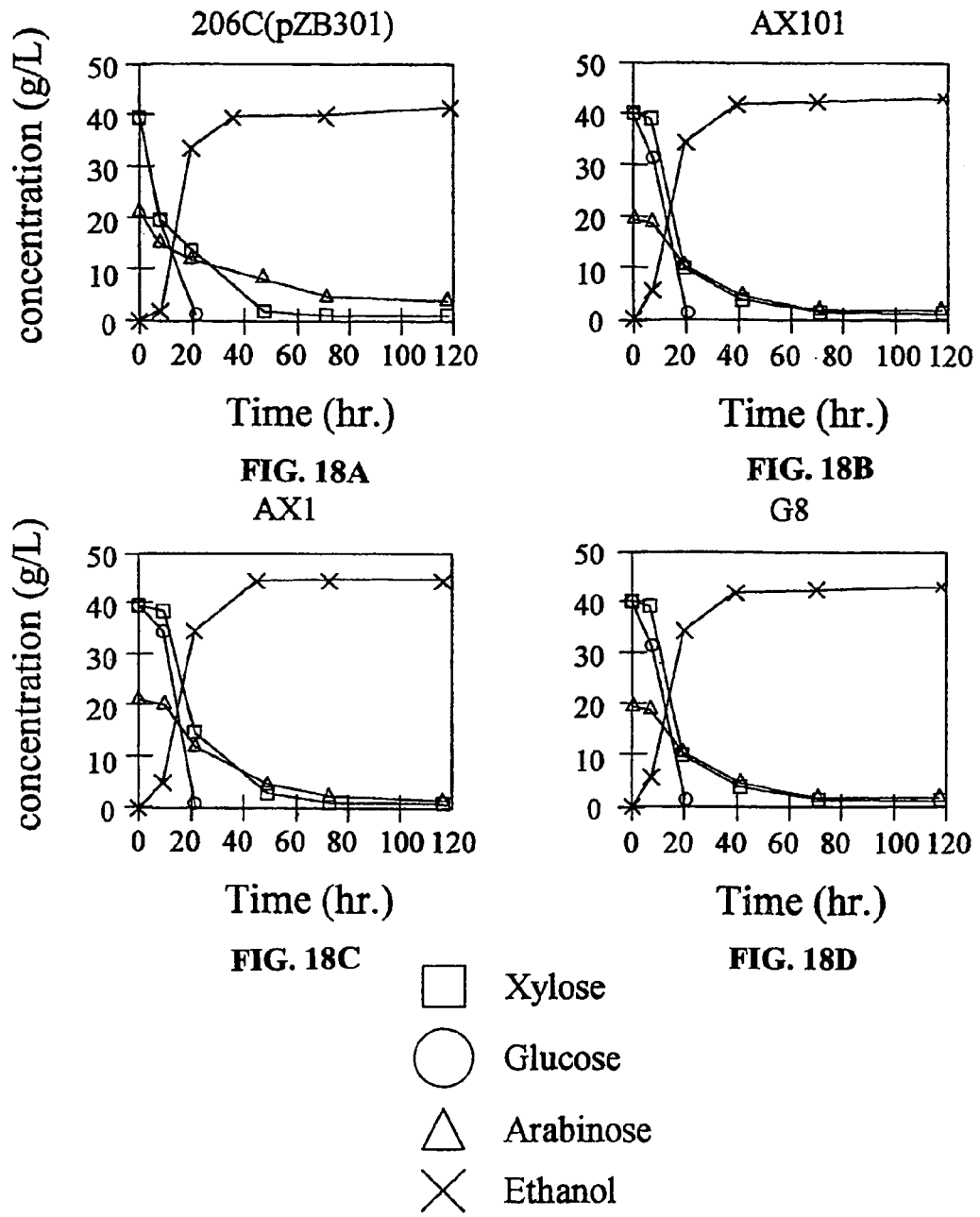
FIGS. 18A-18D is a line graph representation of the fermentation performance of the genomic integrated xylose and arabinose-fermenting Zymomonas strains 206C (pZB301 (18A), AX101 (18B), AX1 (18C), and G8 (18D), in RM containing 4% glucose, 4% xylose and 2% arabinose at pH 5.5 and 30° C.

Several genomic integrated xylose and arabinose fermenting Z. mobilis strains developed through both homologous recombination and transposition were studied for their stability in a non-selective medium (RMG). These strains were cultured in RMG medium and serially transferred, daily, after about 10 generations. After every 40 generations, the cells were used to inoculate a flask containing 1% glucose and 2% xylose and 2% arabinose for examination of their ability to ferment xylose and arabinose to ethanol. Ethanol process yields, and xylose and arabinose utilization rates, were used as the stability trait. Two of the isolates remained stable for 160 generations. See, FIGS. 16 and 17. Three integrated strains and a plasmid-bearing strain were further tested for fermentation performance, in a media containing a mixture of 4% glucose, 4% xylose, and 2% arabinose at pH 5.5 and 30° C. A shown in FIG. 18, all three strains utilized glucose, xylose and arabinose in 72 hours, while the plasmid-bearing strains still had 6 g/L residual arabinose. However, the integrated strains produced more xylitol (4 g/l) than the plasmid bearing strain (1 g/L). The two homologous recombination AX1 and AX101 strains did not produce lactate because the lactate dehydrogenase gene was inactivated through the gene integration. The process yields (about 83% of theoretical) of the integrated strains were very similar to the plasmid bearing strain. Moreover, the integrated strains grew to a greater cell densities, which is probably due to a the lesser metabolic burden associated with having only singly copy of the seven genes.

While the present invention has been described in connection with the illustrated embodiments. It will be appreciated and understood that modifications may be made without departing, from the true spirit and scope of the invention.

The invention claimed is:

1. A vector pZB1862-ldhL-ara ATCC accession no. PTA-1798.
2. A transposable element mini-Tn5-tal/tkt-xylAxxylB ATCC accession no. PTA-1795.
3. A bacterial strain G8 ATCC accession no. PTA-1796.
4. A bacterial strain C25 ATCC accession no. PTA-1799.
5. A bacterial strain AX1 ATCC accession no. PTA-1797.
6. A bacterial strain AX101, ATCC accession no. PTA-4072.

* * * * *